US005672686A

United States Patent [19]
Chittenden

[11] Patent Number: 5,672,686
[45] Date of Patent: Sep. 30, 1997

[54] BCL-Y - SPECIFIC ANTIBODIES

[75] Inventor: Thomas D. Chittenden, Brookline, Mass.

[73] Assignee: ImmunoGen, Inc., Cambridge, Mass.

[21] Appl. No.: 321,071

[22] Filed: Oct. 11, 1994

Related U.S. Application Data

[63] Continuation-in-part of Ser. No. 287,427, Aug. 9, 1994, abandoned.

[51] Int. Cl.$^6$ .............................. C07K 16/18; C12N 5/20
[52] U.S. Cl. .................... 530/387.9; 530/388.2; 530/391.3; 530/389.1; 435/240.27
[58] Field of Search ......................... 424/13.1, 139.1, 424/141.1, 178.1, 1.49; 435/188, 240.27; 530/387.1, 387.2, 387.9, 388.1, 388.2, 389.1, 391.3

[56] References Cited

U.S. PATENT DOCUMENTS 5,015,568  5/1991  Tsujimoto .
5,202,429  4/1993  Tsujimoto .

OTHER PUBLICATIONS

Tsujimoto, et al., Proc. Natl. Acad. Sci., vol. 83, pp. 5214–5218 (1986).
Fisher, et al., Cancer Research, vol. 53, pp. 3321–3326 (1993).
Reed, et al., Analytical Biochemistry. vol. 205, pp. 70–76 (1992).
Bitterman, et al., Repair After Acute Lung Injury, Chest 105(3):118S–121S (1994).
Boise, et al., Bcl-x, A Bcl-2-Related Gene That Functions As A Dominant Regulator of Apoptotic Cell Death, Cell 74:597–608 (1993).
Henderson, et al., Epstein–Barr Virus–Coded BHRF1 Protein, A Viral Homologue of Bcl-2, Protects Human B Cells From Programmed Cell Death, Cell Biology Proc. Natl. Acad. Sci. USA 90:8479–8483 (1993).
Hengartner, et al., Caenorhabditis Elegans Gene Ced-9 Protects Cells From Programmed Cell Death, Nature 356:494–499 (1992).
Hibner, et al., Signaling Of Progrmmed Cell Deth Induction In WEHI–231 B Lymphoma Cells, Eur. J. Immunol. 23(11):2821–2825 (1993).
Hockenbery, et al. BCL2 Protein Is Topographically Restricted In Tissues Characterized By Apoptotic Cell Death, Proc. Natl. Acad. Sci. USA 88:6961–6965 (1991).
Korsmeyer, et al., Bcl-2/Bax: A Rheostat That Regulates an Anti–Oxidant Pathway And Cell Death, Cancer Biology 4:327–332 (1993).
Kozopas, et al., MCL1, A Gene Expressed In Programmed Myeloid Cell Differentiation, Has Sequence Similarity To BCL2, Proc. Natl. Acad. Sci. USA 90:3516–3520 (1993).
Oltvai, et al., Bcl-2 Heterodimerizes In Vivo With A Conserved Homolog, Bax, That Accelerates Programed Cell Death, Cell 74:609–619 (1993).
Carson, et al., Apoptosis And Disease, The Lancet 341:1251–1254 (1993).
Rees, et al., Antisense-Mediated Inhibition Of BCL2 Protooncogene Expression And Leukemic Cell Growth Survival: Comprison Of Phosphodiester And Phosphorothioate Oligodeoxynucleotides, Cancer Research 50:6565–6570 (1990).
Yin, et al., BH1 And BH2 Domains Of Bcl-2 Are Required For Inhibitoin Of Apoptosis And Heterodimerization Wtih Bax, Nature 369:321–323 (1994).
Williams, Programmed Cell Death: Apoptosis And Oncogenesis, Cell 65:1097–1098 (1991).
Lin, et al., Characterization Of A1, A Novel Hemopoietic–Specific Early–Response Gene With Sequence Similarity To Bcl-2, The Journal of Immunology 151:1979–1988 (1993).
Neilan, et al., An African Swine Fever Virus Gene With Similarity To The Proto–Oncogene Bcl-2 And The Epstein–Barr Virus Gene BHRF1, Journal of Virology 67:4391–4394 (1993).
Campos, et al., Effects of BC1-2 Antisenses Oligodeoxy-nucleotides On In Vitro Proliferation And Survival Of Normal Marrow Progenitors And Leukemic Cells, Blood 84:595–600 (1994).
Williams, et al., Molecular Regulation of Apoptosis: Genetic Controls On Cell Death, Cell 74:777–779 (1993).
Fanidi, et al., Coperative Interaction Between C–myc And Bcl-2 Proto–Oncogenes, Nature 359:554–556 (1992).
Hengartner, et al., C Elegans Cell Survival Gene Ced-9 Encodes A Functional Homolog Of The Mammaloian Proto–Oncogene Bcl-2, Cell 76:665–676 (1994).
Vaux, et al., Prevention Of Programmed Cell Dath In Caenorhabditis Elegans By Human Bcl-2, Science 258:1955–1957 (1992).
Hockenbery, et al., Bcl-2 Is An Inner Mitochondrial Membrane Protein That Blocks Programmed Cell Death, Nature 348:334–336 (1990).

(List continued on next page.)

Primary Examiner—Paula K. Hutzell
Assistant Examiner—Nancy A. Johnson
Attorney, Agent, or Firm—Hale and Dorr

[57] ABSTRACT

The present invention is directed to an isolated Bcl-Y protein, nucleotide sequences coding for and regulating expression of the protein, antibodies directed against the protein, and recombinant vectors and host cells containing the genetic sequences coding for and regulating the expression of the protein sequence. The invention is also directed to genomic DNA, cDNA, and RNA encoding the Bcl-Y protein sequence and to corresponding antisense RNA sequences. Antibodies can be used to detect Bcl-Y in biological specimens, including, for example, human tissue samples. The present invention is further directed to methods of treating degenerative disorders characterized in inappropriate cell proliferation or inappropriate cell death. The present invention is further directed to methods for diagnosing degenerative disorders characterized in inappropriate cell proliferation or inappropriate cell death, as well as methods for monitoring the progress of such degenerative disorders.

6 Claims, 16 Drawing Sheets

OTHER PUBLICATIONS

Evan, et al., Induction Of Apoptosis In Fibroblasts By C–myc Protein, *Cell* 69:119–128 (1992).

Harrington, et al., C–Myc–Induced Apoptosis In Fibroblasts Is Inhibited By Specific Cytokines, *The EMBO Journal* 13:3286–3295 (1994).

Reed, Bcl–2 And The Regulation Of Programmed Cell Death, *J. Cell Biol.* 124:1–6 (1994).

Tanaka, et al., Cellular Commitment To Oncogene–Induced Trasnformation Or Apoptosis Is Dependent On The Transcription Factor IRF–1, *Cell* 77:829–839 (1994).

Rao, et al., The Adenovirus E1A Proteins Induce Apoptosis, Which Is Inhibited By The E1B 19–kDa And Bcl–2 Proteins, *Proc. Natl. Acad. Sci. USA* 89:7742–7746 (1992).

Wu, et al., P53 And E2F–1 Cooperate To Mediate Apoptosis, *Proc. Natl. Acad. Sci. USA* 91:3602–3606 (1994).

```
                                    I
BCL-2   E E L F R D G . V N W G R I V A F F E F G G V M C V E S V N R E M S P L
BCL-X   N E L F R D G . V N W G R I V A F S F G G A L C V E S V D K E M Q V L
BAX     A D M F S D G N F N W G R I V A L F Y F A S K L V L K A L C T K V P E L
MCL-1   I H V F S D G V T N W G R I V T L I S F G A F V A K H L K T I N Q E S C
A1      E K E F E D G I I N W G R I V T I E A F G G V L L K K L P Q E Q I A L D
ASFV    T E L F K D L . I N W G R I C G F I V E S A R M

| | | | | | | | | | | |
|---|---|---|---|---|---|---|---|---|---|---|
| BCL-Y | | | | NWGRVVALLGFGYRLALHVYQHGLTGF | | | LGQVTRFVVDFMLHHCIAR | WIAQRGGW . DAFVELY | 202 | [SEQ ID NO. 15] |
| BCL-2 | EELFRDG . | VNWGRIVAFFEFGGVMCVESVNRDKESVPL | | | | | VDNIALWMTEYLNRHLHT . | WIQDNGGW . DAFVELY | 195 | [SEQ ID NO. 6] |
| BCL-X | NELFRDG . | VNWGRIVAFFSFGGALCVEESVDKEMQVL | | | | | VSRIAAWMATYLNDHLEP . | WIQENGGW . DTFVELY | 165 | [SEQ ID NO. 7] |
| BAX | ADMFSDGN | NWGRVVALFYFGGALCVLKALCTKVPEL | | | | | IRTIMGWTLDFLLRERLLG | WIQDQGGW . DGLLSYF | 319 | [SEQ ID NO. 8] |
| MCL-1 | IHVFSDGV | NWGRIVTLISFGAFVAKHLKTINQESC | | | | | IEPLAESITDVLVRTKRD . | WLVKQRGW . DGFIKKF | 148 | [SEQ ID NO. 9] |
| A1 | EKEFEDGI | NWGRIVTIFAFGGVLLKKLPQEQIALD | | | | | VCAYKQVSSFVAEFIMNTGE | WIRQNGGW . EDGFVEF | 141 | [SEQ ID NO. 10] |
| ASFV | TELFKDL . | NWGRICCFIVFSARMAKYCKDANNHLE | | | | | STVITTAYNFMKHNLLP . | WMISHGGQ . EEFLAFS | 157 | [SEQ ID NO. 11] |
| EBV | LEIFHRGD | PSLGRALAWCMHACRTLCCNQSTPY | | | | | YVVDLSVRGMLEASEGLDG | WIHQQGGW . STLIEDN | | [SEQ ID NO. 12] |

FIG.1B

```
TGAGCCACCC GGGTTGGGCC AGGATCCCGG CAGGCTGATC CCGTCCTCCA CTGAGACCTG        60

AAAAATGGCT TCGGGGCAAG GCCCAGGTCC TCCCAGGCAG GAGTGCGGAG AGCCTGCCCT       120
     M  A   S  G  Q    G  P  G  P    P  R  Q    E  C  G  E    S  L  P

GCCCTCTGCT TCTGAGGAGC AGGTAGCCCA GGACACAGAG GAGGTTTTCC GCAGCTACGT       180
  P  S  A   S  E  E    Q  V  A  Q    D  T  E    E  V  F    R  S  Y  V

TTTTTACCGC CATCAGCAGG AACAGGAGGC TGAAGGGGTG GCTGCCCCTG CCGACCCAGA       240
  F  Y  R   H  Q  Q    E  Q  E  A    E  G  V    A  A  P    A  D  P  E

GATGGTCACC TTACCTCTGC AACCTAGCAG CACCATGGGG CAGGTGGGAC GGCAGCTCGC       300
  M  V  T   L  P  L    Q  P  S  S    T  M  G    Q  V  G    R  Q  L  A

CATCATCGGG GACGACATCA ACCGACGCTA TGACTCAGAG TTCCAGACCA TGTTGCAGCA       360
  I  I  G   D  D  I    N  R  R  Y    D  S  E    F  Q  T    M  L  Q  H

CCTGCAGCCC ACGGCAGAGA ATGCCTATGA GTACTTCACC AAGATTGCCA CCAGCCTGTT       420
  L  Q  P   T  A  E    N  A  Y  E    Y  F  T    K  I  A    T  S  L  F

TGAGAGTGGC ATCAATTGGG GCCGTGTGGT GGCTCTTCTG GGCTTCGGCT ACCGTCTGGC       480
  E  S  G   I  N  W    G  R  V  V    A  L  L    G  F  G    Y  R  L  A

CCTACACGTC TACCAGCATG GCCTGACTGG CTTCCTAGGC CAGGTGACCC GCTTCGTGGT       540
  L  H  V   Y  Q  H    G  L  T  G    F  L  G    Q  V  T    R  F  V  V

CGACTTCATG CTGCATCACT GCATTGCCCG GTGGATTGCA CAGAGGGGTG GCTGGGTGGC       600
  D  F  M   L  H  H    C  I  A  R    W  I  A    Q  R  G    G  W  V  A

AGCCCTGAAC TTGGGCAATG GTCCCATCCT GAACGTGCTG GTGGTTCTGG GTGTGGTTCT       660
  A  L  N   L  G  N    G  P  I  L    N  V  L    V  V  L    G  V  V  L

GTTGGGCCAG TTTGTGGTAC GAAGATTCTT CAAATCATGA                             700
  L  G  Q   F  V  V    R  R  F  F    K  S  *       [SEQ ID NO. 16]
```

FIG.4A

```
                                              CTCCCAAGGG TGCCCTTTGG    720
GTCCCGGTTC AGACCCTGC CTGGACTTAA GCGAAGTCTT TGCCTTCTCT GTTCCCTTGC    780
AGGGGTCCCC CCTCAAGAGT ACAGAAGCTT TAGCAAGTGT GCACTCCAGC TTCGGAGGGC    840
CCCTGCGTGG GGGCCAGTCA GGCTGCAGAG GCACCTCAAC ATTGCATGGT GCTAGTGGGC    900
CCTCTCTCTG GGCCCAGGGG CTGTGGCCGT CTCCTCCCTC AGCTCTCTGG GACCTCCTTA    960
GCCCTGTCTG CTAGGCGCTG GGAGACTGA TAACTTGGGG AGGCAAGAGA CTGGGAGCCA    1020
CTTCTCCCCA GAAAGTGTTT AACGGTTTTA GCTTTTTATA ATACCCTTGT GAGAGCCCAT    1080
TCCCACCATT CTACCTGAGG CCAGGACGTC TGGGTGTGG GGATTGGTGG GTCTATGTTC    1140
CCCAGGATTC AGCTATTCTG GAAGATCAGC ACCCTAAGAG ATGGGACTAG GACCTGAGCC    1200
TGGTCCTGGC CGTCCCTAAG CATGTGTCCC AGGAGCAGGA CCTACTAGGA GAGGGGGGCC    1260
AAGGTCCTGC TCAACTCTAC CCCTGCTCCC ATTCCTCCCT CCGGCCATAC TGCCTTTGCA    1320
GTTGGACTCT CAGGGATTCT GGGCTTGGGG TGTGGGGTGG GGTGGAGTCG CAGACCAGAG    1380
CTGTCTGAAC TCACGTGTCA GAAGCCTCCA AGCCTGCCTC CCAAGGTCCT CTCAGTTCTC    1440
TCCCTTCCTC TCTCCTTATA GACACTTGCT CCCAACCCAT TCACTACAGG TGAAGGCTCT    1500
CACCCCATCC CTGGGGGCCT TGGGTGAGTG GCCTGCTAAG GCTCCTCCTT GCCCAGACTA    1560
CAGGGCTTAG GACTTGGTTT GTTATATCAG GGAAAAGGAG TAGGGAGTTC ATCTGGAGGG    1620
TTCTAAGTGG GAGAAGGACT ATCAACACCA CTAGGAATCC CAGAGGTGGG ATCCTCCCTC    1680
ATGGCTCTGG CACAGTGTAA TCCAGGGGTG TAGATGGGGG AACTCTGAAT ACTTGAACTC    1740
TGTTCCCCCA CCCTCCATGC TCCTCACCTG TCTAGGTCTC CTCAGGGTGG GGGTGACAG    1800
TGCCTTCTCT ATTGGGCACA GCCTAGGGTC TTGGGGGTCA GGGGGGAGAA GTTCTTGATT    1860
CAGCCAAATG CAGGGAGGGG AGGCAGATGG AGCCCATAGG CCACCCCCTA TCCTCTGAGT    1920
GTTTGGAAAT AAACTGTGCA ATCCCCTCAC CCTGAAAAAA AAAAAAAA [SEQ ID NO. 17]    1968
```

FIG.4B

BCL-2   60   A A S R D P V A R T S P L Q T P A A P G [SEQ ID NO. 18]
BCL-Y   53   A A P A D P E M V T L P L Q P S S T M G [SEQ ID NO. 19]

BCL-2  101   G D D F S R R Y R G D F A E M S S Q L H L T P F T A R G R F A T V V E E L F R D G V N W G R I V A F F E F G [SEQ ID NO. 20]
BCL-Y   82   G D D I N R R Y D S E F Q T M L Q H L Q P I A E N A Y E Y F T K I I A T S L F E S G I N W G R V V A L L G F G [SEQ ID NO. 21]

BCL-2  181   L N R H L H T W I Q D N G G W D A F V E L [SEQ ID NO. 22]
BCL-Y  163   L H H C I A R W I A Q R G G W D A A I N L [SEQ ID NO. 23]

BCL-Y - SPECIFIC ANTIBODIES

CROSS REFERENCE TO RELATED APPLICATIONS

This application is a continuation-in-part of U.S. application Ser. No. 08/287,427, filed 9 Aug. 1994 (abandoned).

FIELD OF THE INVENTION

The present invention relates generally to the field of cell physiology, and more particularly, to apoptosis. Even more particularly, the present invention is related to the novel apoptosis associated protein Bcl-Y; to nucleotide sequences encoding Bcl-Y; to products and processes involved in the cloning, preparation and expression of genes and nucleotide sequences encoding Bcl-Y; to antibodies with specificity to Bcl-Y; and to diagnostic and therapeutic uses of the above.

BACKGROUND OF THE INVENTION

Apoptosis refers to cell suicide that proceeds by an active, physiological process (Kerr, J. F., et al., Br. J. Cancer 26:239–257 (1972); Wyllie, A. H., Nature 284:555–556 (1980)). Cells that die by apoptosis undergo characteristic morphological changes, including cell shrinkage, and nuclear condensation and fragmentation. Apoptosis plays an important role in developmental processes, including morphogenesis, maturation of the immune system, and tissue homeostasis whereby cell numbers are limited in tissues that are continually renewed by cell division (Ellis, R. E., et al., Annu. Rev. Cell. Biol. 7:663–698 (1991); Oppenheim, R. W., et al., Neurosci. 14:453–501 (1991); Cohen, J. J., et al., Annu. Rev. Immunol. 10:267–293 (1992); Raff, M. C., Nature 356:397–400 (1992)). While the cell death program can be activated through a diversity of normal physiological stimuli, cells also die by apoptosis following a variety of non-physiological insults, including irradiation and exposure to DNA damaging drugs (Eastman, A., Cancer Cells 2:275–280 (1990); Dive, C., et al., Br. J. Cancer 64:192–196 (1991); Lennon, S. V., et al., Cell prolif. 24:203–214 (1991)).

In addition to its role in developmental processes, apoptosis is an important cellular safeguard against tumorigenesis (Williams, G. T., Cell 65:1097–1098 (1991); Lane, D. P. Nature 362:786–787 (1993)). Defects in the apoptotic pathway may contribute to the onset or progression of malignancies. Under certain conditions, cells undergo apoptosis in response to forced expression of oncogenes, or other genes that drive cell proliferation; (Askew, D., et al., Oncogene 6:195–1922 (1991); Evan, G. I., et al., Cell 69:119–128 (1992); Rao, L., et al., Proc. Natl. Acad. Sci. USA 89:7742–7746 (1992); Smeyne, R. J., et al., Nature 363:166–169 (1993)). The potential importance of apoptosis as a defense against tumorigenesis is underscored by the observation that suppression of the apoptotic pathway(s), by a variety of genetic lesions, occurs frequently in a broad range of human tumors. As a specific example, loss of the p53 tumor suppressor gene function, either through deletion or mutation, occurs in more than 50% of human cancers (Levine, A. J., et al., Nature 351:453–456 (1991); Lane, D. P. Nature 362:786–787 (1993)). The p53 protein is required for efficient induction of apoptosis by DNA damaging agents (including irradiation and most chemotherapeutic drugs) (Clark, A. R., et al., Nature 362:849–852 (1993); Lowe, S. W., et al., Cell 74:957–967 (1993a); Lowe, S. W., et al., Nature 362:847–849 (1993b)). This activity is likely to be at least part of the tumor suppressor function of p53. Cells that suffer extensive, and potentially carcinogenic, genetic damage may self destruct via a p53 dependent mechanism thereby reducing the potential for tumorigenesis (Lane, D. P. Nature 362:786–787 (1993)).

In addition to cancer, deregulation of apoptosis may contribute to a number of other human diseases. A variety of degenerative disorders may involve aberrant apoptosis, resulting in premature or inappropriate cell death (Barr, P. J., et al., Biotechnology 12:487–493 (1994)). Productive infection by certain viruses may depend on suppression of host cell death by anti-apoptotic viral gene products (Rao, L., et al., Proc. Natl. Acad. Sci. USA 89:7742–7746 (1992); Ray, C. A., et al., Cell 69:597–604 (1992); White, E., et al., Mol. Cell. Biol. 12:2570–2580 (1992); Vaux, D. L., et al., Cell 76:777–779 (1994), and inhibition of apoptosis can alter the course (i.e. lytic vs. latent) of viral infection; Levine, B., et al., Nature 361:739–742 (1993)). Widespread apoptosis of T lymphocytes triggered by HIV infection may, at least in part, be responsible for the immune system failure associated with AIDS (Gougeon M., et al., Science 260:1269–1270 (1993)). Therefore, from the perspective of pharmaceutical development, it would be desirable to identify or develop agents that either activate, or suppress, apoptosis depending on the clinical setting.

The bcl-2 gene product has been intensively studied as a potent suppressor of apoptotic cell death. The bcl-2 gene was originally identified at the t(14:18) translocation breakpoint that occurs frequently in human B cell follicular lymphomas (Bakhshi, A., et al., Cell 41:899–906 (1985); Cleary, M. L., et al., Proc. Natl. Acad. Sci. USA 82: (1985); Tsujimoto, Y., et al., Science 229:1390–1393 (1985)). This translocation results in the constitutive activation of bcl-2 gene expression due to juxtaposition with the immunoglobulin heavy chain locus. Bcl-2 functions as an oncogene in this disease by inappropriately suppressing apoptosis that would normally limit the accumulation of these cells (McDonnell, T. J., et al., Cell 57:79–88 (1989); Hockenbery, D., et al., Nature 348:334–336 (1990)). Consequently, B cells accumulate during the indolent stage of the lymphoma due to their failure to die rather than by uncontrolled proliferation.

Targeted gene disruption experiments indicate that one important normal function of Bcl-2 is to contribute to the maintenance and survival of the mature immune system (Nakayama, K., et al., Science 261:1584–1588 (1993); Veis, D. J., et al., Cell 75:229–240 (1993)). However, the anti-apoptotic activity of Bcl-2 is not restricted to B cells. A large number of studies have demonstrated that ectopic Bcl-2 expression can suppress apoptosis triggered by diverse stimuli in a multitude of cell lineages (Vaux, D. L., et al., Nature 335:440–442 (1988); Sentman, C. L., et al., Cell 67:879–888 (1991); Strasser, A., et al., Cell 67:889–899 (1991); Hockenbery, D. M., et al., Cell 75:241–251 (1993)). Bcl-2 blocks cell death induced by growth factor withdrawal, DNA damage, oncogene expression, oxidative stress, viral infection. The ability of Bcl-2 to block apoptosis in virtually every system suggests that Bcl-2 is closely connected with the machinery that actually carries out the death program. This view is further supported by the conservation of Bcl-2 function across species. The ced9 gene in the nematode c. Elegans functions to suppress programmed death in certain cell lineages of the developing worm (Ellis, H. M., et al., Cell 44:817–829 (1986)). Ced9 appears to be a functional homologue of Bcl-2, since Bcl-2 can complement ced9 in transgenic worms (Vaux, D. L., et al., Science 258:1955–1957 (1991)). Bcl-2 can also function in insect cells as demonstrated by the ability of Bcl-2 to suppress apoptosis induced by Baculovirus infection (Alnemri, E. S., et al., Proc. Natl. Acad. Sci. USA 89:7295–7299 (1992)).

The molecular mechanism whereby Bcl-2 operates to block cell death is poorly understood. Bcl-2 is a 25 kD membrane associated protein that has been detected in mitochondrial membranes, the nuclear envelope, and the endoplasmic reticulum (Chen-Levy, et al., Mol. Cell. Biol. 9:701–710 (1989); Hockenbery, D., et al., Nature 348:334–336 (1990); Jacobson, et al., Nature 361:365–369 (1993)). Bcl-2 has been found to physically associate with the ras related protein r-Ras (Fernandez-Sarabia, et al., Nature 366:274–275 (1993)). However, the biological significance of this interaction is still uncertain. Several lines of evidence have suggested that Bcl-2 functions in an antioxidant pathway, although it is not clear whether this is a direct or indirect activity of Bcl-2 (Hockenbery, D. M., et al., Cell 75:241–251 (1993); Kane, D. J., et al., Science 262:1274–1277 (1993); Butte, T. M., et al., Immunol. Today 15:7–10 (1994)).

Additional cellular Genes that exhibit significant sequence homology with Bcl-2 have recently been identified and, where tested, these Genes appear also to function as regulators of apoptotic cell death. One Bcl-2 relative, Bcl-X, was isolated by low stringency DNA hybridization to the Bcl-2 gene (Boise, L. H., et al., Cell 74:597–608 (1993)). The Bcl-X RNA is differentially spliced to produce a long form, termed Bcl-$X_L$, and a shorter form, Bcl-$X_S$, bearing a short internal deletion. Bcl-$X_L$ functions to suppress cell death, much like Bcl-2, whereas the deleted form, Bcl-$X_S$, can inhibit protection by Bcl-2 and may function as a "dominant negative" species. A second Bcl-2 relative, Bax, was identified biochemically as protein found in co-immunoprecipitates with Bcl-2 (Oltvai, Z. N., et al., Cell 74:609–619 (1993)). Isolation of the corresponding cDNA revealed that the Bax protein shows substantial sequence homology to Bcl-2. Bax forms heterodimers with Bcl-2 and appears to induce apoptosis and function as a negative regulator of Bcl-2 function. Ectopic expression of Bax was shown to block the protection against apoptosis afforded by Bcl-2 expression.

Two additional cellular Bcl-2 relatives, Mcl and A1 (Kozopas, K. M., et al., Proc. Natl. Acad. Sci. USA 90:3516–3520 (1993); Lin, E. Y., et al., J. Immunol. 151:1979–1988 (1993)) were originally isolated as mRNAs induced in response to specific stimuli: phorbol ester induced differentiation of myeloid leukemia cells (Mcl) and GM-CSF treatment of murine bone marrow cells (A1). It is not yet known whether either Mcl or A1 can modulate apoptosis.

In addition to these cellular Bcl-2 relatives, a number of Bcl-2 homologues encoded by DNA viruses have been identified. The Epstein-Barr virus BHRF-1 gene product was noted to contain sequence homology to Bcl-2 and has subsequently been shown to function as a suppressor of apoptosis (Henderson, et al., Proc. Natl. Acad. Sci. USA 90:8479–8488 (1993)). Likewise, the African swine fever virus LMW5-HL gene encodes a protein structurally similar to Bcl-2 (Neilan, J. G., et al., J. Virol. 67:4391–4394 (1993)). The Adenovirus E1b 19 kD protein appears to be functionally equivalent to Bcl-2, although the primary sequence homology is quite limited (White, E., et al., Mol. Cell. Biol. 12:2570–2580 (1992)). It is likely that these genes function to ensure replication of viral DNA by preventing apoptosis of the infected cell. The finding that unrelated DNA viruses have evolved genes that apparently function to mimic the action of Bcl-2, supports the conclusion that Bcl-2 represents an important apoptosis regulator.

The five known cellular Bcl-2 related genes, where analyzed, have distinct patterns of expression and thus may function in different tissues. The cell death program is in place in all tissues and may be regulated by different Bcl-2 related genes. While Bcl-2 expression is required for maintenance of the mature immune system, it is desirable to identify other genes which may govern apoptotic cell death in other lineages.

SUMMARY OF THE INVENTION

The present inventor has surprisingly discovered a novel composition of matter which has been isolated and characterized, and which is described in a number of embodiments herein. Referred to herein as "Bcl-Y," it appears to be a member of the Bcl-2 family, and can, inter alia, induce apoptosis in cells and function as a negative regulator of Bcl-2 function in cells. Isolation of a full length human Bcl-Y cDNA revealed that the deduced Bcl-Y amino acid sequence shares the most homology with Bcl-2, with additional regions of homology extending outside of domains I and II. Bcl-Y mRNA was detected in all human tumor cell lines examined, and appears to be widely expressed in primary human tissues. In view of its widespread expression and significant homology to Bcl-2, Bcl-Y is an important regulator of apoptosis in human tissues and/or tumor cells.

Bcl-Y by itself accelerates apoptosis when expressed in FL5.12 cells, an IL-3 dependent murine cell line that undergoes apoptosis upon cytokine withdrawal (Hockenbery, D., et al., Nature 348:334–336 (1990)). Also, when Bcl-Y is expressed in FL5.12 cells that are over-expressing an exogenous Bcl-2 clone, the presence of Bcl-Y reduces the protective effect of Bcl-2 under conditions designed to induce apoptosis in those cells.

The present invention thus relates to an apoptosis associated protein Bcl-Y, products and processes involved in the cloning, preparation and expression of genes for Bcl-Y; antibodies with specificity to Bcl-Y; and nucleotide probes corresponding to the Bcl-Y nucleotide sequence or portions thereof. The Bcl-Y polypeptide is useful for producing antibodies thereto. The antibodies and probes are useful for detecting and isolating Bcl-Y in biological specimens including for example, cells from all human tissues including heart tissue, lung tissue, tumor cells, brain tissue, placenta, liver, skeletal muscle, kidney, and pancreas.

The present invention further relates to species homologs and viral homologs of Bcl-Y.

The present invention relates to the identification, characterization and sequencing of cDNAs and genomic fragments which encode the Bcl-Y that is present in human cells.

According to the present invention, there are provided genetic sequences encoding Bcl-Y. The instant invention also provides for expression vectors containing such genetic sequences, hosts transformed with such expression vectors, and methods for producing the genetically engineered or recombinant Bcl-Y.

The present invention also provides antibodies which specifically recognize Bcl-Y.

The Bcl-Y cDNA and recombinant protein are useful for making antibodies which specifically recognize Bcl-Y. Such antibodies are useful for detecting and isolating Bcl-Y in a biological specimen. The present Bcl-Y protein is also useful as a regulator of apoptosis.

A small cDNA from the Namalwa, ATCC CRL 1432, human B-cell lymphoma cell line, and from the human leukemia cell line U937 ATCC CRL 1593, has been isolated. The amino acid sequence of the Bcl-Y protein shares sequence homology with Bcl-2, with additional regions of homology extending outside of domains I and II.

The present invention further relates to a method for isolating Bcl-Y partial clones using polymerase chain reaction (PCR) cloning, from diverse human tumor cell lines.

The present invention is further directed to methods for inducing or suppressing apoptosis in individuals suffering from degenerative disorders characterized by inappropriate cell proliferation or inappropriate cell death, respectively. Degenerative disorders characterized by inappropriate cell proliferation include, for example, inflammatory conditions, cancer, including lymphomas, genotypic tumors, etc. Degenerative disorders characterized by inappropriate cell death include, for example, autoimmune diseases, acquired immunodeficiency disease (AIDS), cell death due to radiation therapy or chemotherapy, etc.

The present invention also relates to methods for detecting the presence of Bcl-Y protein, as well as methods directed to the diagnosis of degenerative disorders, which disorders are associated with an increased or decreased level of expression of Bcl-Y, as compared to the expected level of Bcl-Y expression in the normal cell population.

The present invention is further directed to methods for monitoring the progress of degenerative disorders associated with increased or decreased levels of expression of Bcl-Y, by monitoring Bcl-Y expression.

The present invention also relates to methods for determining whether a disease/degenerative disorder is linked to abnormal Bcl-Y expression, as well as methods for determining the effect of over expression or loss of expression of Bcl-Y in animal models such as transgenic mice and/or homozygous null mice. Methods for determining whether a disease/degenerative disorder is linked to abnormal Bcl-Y expression include analyzing Bcl-Y expression in diseased tissue as compared to normal tissue by for example, Northern and/or Western blots, as well as by other assay methods readily chosen and employed by those of ordinary skill in the art.

The present invention relates to hybrids of Bcl-Y for therapeutic use.

The present invention also relates to methods for modulating apoptotic effects by administering the present Bcl-Y protein, mutant protein or hybrids to an individual suffering from a degenerative disorder characterized by inappropriate cell proliferation or inappropriate cell death in order to stabilize inappropriate cell proliferation (i.e., induce apoptosis) or stabilize inappropriate cell death (i.e., suppress apoptosis), respectively, and/or in either case to restore normal cell behavior. FIG. 8 illustrates levels of Bcl-Y mRNA expressed in a variety of healthy adult tissues.

The present invention further relates to functional equivalents including functional fragments of Bcl-Y including, for example, peptides of Bcl-Y such as Domain I and Domain II, and other regions of homology recognized by the present inventor between Bcl-Y and other apoptosis related proteins including Bcl-2 and Bax.

The present invention is also directed to nucleotide probes which can be used to determine the presence of Bcl-Y as well as to identify and isolate homologs including species homologs and viral homologs.

DESCRIPTION OF THE FIGURES

FIG. 1. Conservation of domains I and II among Bcl-2 family members.

FIG. 1(A). Amino acid sequence homology between previously known Bcl-2 homologues. Degenerate PCR primers (BD2 and BU3), corresponding to conserved domains I and II (boxed), are shown at bottom. ASFV and EBV refer to the African swine fever virus LMW5-HL and Epstein-Barr virus BHRF1 genes, respectively. The numbers at the far right refer to the amino acid position number in the corresponding proteins.

FIG. 1(B). Conceptual translation of the Bcl-Y fragment isolated by PCR. The Bcl-Y PCR product obtained with primers BD2 and BU3 is shown on the top line. The underlined residues correspond to the primers used in PCR. The shaded, bold faced residues are sequence elements highly conserved among the previously identified Bcl-2 relatives.

FIG. 4. DNA sequence and conceptual translation of a composite Bcl-Y cDNA. The initiating methionine codon is shown in bold face, and is preceded by stop codons (underlined) in all three reading frames.

FIG. 5. Homology of Bcl-Y to Bcl-2. The three regions of Bcl-Y with the highest homology to Bcl-2 are shown. The homology and alignments were performed by the BLASTP program. Boxed, shaded residues indicate identity, lightly shaded residues indicate conservative changes.

FIG. 6. Alignment of Bcl-Y with the Bcl-2 family. The amino acid positions of the various Bcl-2 relatives are indicated. Boxed, shaded residues are identical in at least 4 of the 8 Bcl-2 relatives. Lightly shaded residues indicate coservative amino acid changes. The hydrophobic C-terminal, putative membrane localization sequences, are underlined.

FIG. 7. Expression of the Bcl-Y protein.

FIG. 9. Effect of Bcl-y expression on viability of FL5.12 cells following IL-3 withdrawal.

FIG. 10. Effect of Bcl-Y expression in FL5.12 cell populations also expressing Bcl-2.

FIG. 11. Effect of Bcl-Y expression in FL5.12 clones also expressing Bcl-2.

DETAILED DESCRIPTION OF THE INVENTION

I. Definitions

Figure 2:
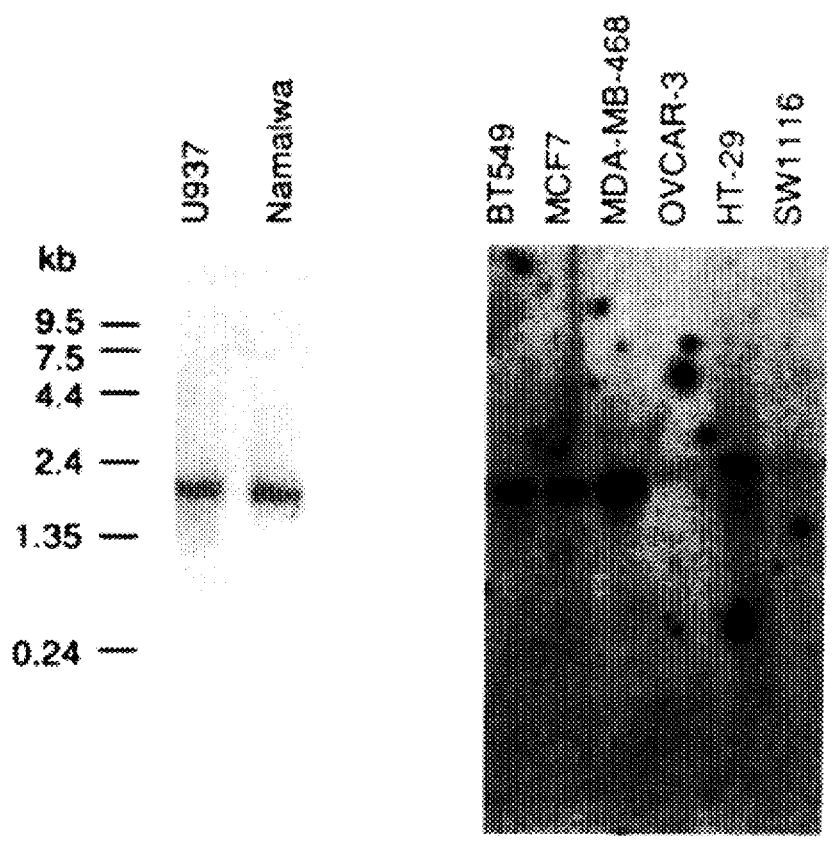
FIG. 2. Expression of the Bcl-Y RNA in tumor cell lines. Northern blot analysis was performed using mRNA prepared from the indicated tumor cell lines. The blots were hybridized with a 32-P labeled probe derived from the Bcl-Y PCR product. RNA size markers (Gibco/BRL) were visualized by ethidium bromide staining.

To aid in the understanding of the specification and the claims, the following definitions are provided:

Gene. By the term "gene" is intended a DNA sequence which encodes through its template or messenger RNA a sequence of amino acids characteristic of a specific peptide. Further, the term includes intervening, non-coding regions, as well as regulatory regions, and can include 5' and 3' ends.

Gene sequence. The term "gene sequence" is intended to refer generally to a DNA molecule. As used herein, the terminology is meant to include both a DNA molecule which contains a non-transcribed or non-translated sequence. The term is further intended to include any combination of gene(s), gene fragment(s), non-transcribed sequence(s), or non-translated sequence(s) which are present on the same DNA molecule.

The present sequences may be derived from a variety of sources including DNA, cDNA, synthetic DNA, RNA, or combinations thereof. Such gene sequences may comprise genomic DNA which may or may not include naturally occurring introns. Moreover, such genomic DNA may be obtained in association with promoter regions or poly A sequences. The gene sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

cDNA. The term "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector. This term includes genes from which the intervening sequences have been removed.

Recombinant DNA. By the term "recombinant DNA" is meant a molecule that has been recombined by in vitro splicing cDNA or a genomic DNA sequence.

Cloning. By the term "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

cDNA Library. By "cDNA library" is meant a collection of recombinant DNA molecules containing cDNA inserts which together comprise the entire genome of an organism. Such a cDNA library may be prepared by methods known to those of skill, and described, for example, in Maniatis, et al., *Molecular Cloning: A Laboratory Manual*, Cold Spring Harbor Laboratories, Cold Spring Harbor, N.Y., 2d. ed. (1989). Generally, RNA is first isolated from the cells of an organism from whose genome it is desired to clone a particular gene. Preferred for the purposes of the present invention are mammalian, and particularly human, cell lines.

Cloning Vehicle. A plasmid or phage DNA or other DNA sequence which is able to replicate in a host cell. The cloning vehicle is characterized by one or more endonuclease recognition sites at which such DNA sequences may be cut in a determinable fashion without loss of an essential biological function of the DNA, which may contain a marker suitable for use in the identification of transformed cells. Markers may include for example, tetracycline resistance or ampicillin resistance. The word "vector" can be used to connote a cloning vehicle.

Expression Control Sequence. An "expression control sequence" is a sequence of nucleotides that controls or regulates expression of structural genes when operably linked to those genes. These include, for example, the lac systems, the trp system major operator and promoter regions of the phage lambda, the control region of fd coat protein and other sequences known to control the expression of genes in prokaryotic or eukaryotic cells. Expression control sequences will vary depending on whether the vector is designed to express the operably linked gene in a prokaryotic or eukaryotic host, and may contain transcriptional elements such as enhancer elements, termination sequences, tissue-specificity elements, and/or translational initiation and termination sites.

Expression vehicle. An "expression vehicle" is a vehicle or vector similar to a cloning vehicle but which is capable of expressing a gene which has been cloned into it, after transformation into a host. The cloned gene is usually placed under the control of (i.e., operably linked to) an expression control sequence.

Operator. A DNA sequence capable of interacting with the specific repressor, thereby controlling the transcription of adjacent gene(s).

Promoter. The term "promoter" is intended to refer to a DNA sequence which can be recognized by an RNA polymerase. The presence of such a sequence permits the RNA polymerase to bind and initiate transcription of operably linked gene sequences.

Promoter region. The term "promoter region" is intended to include the promoter as well as other gene sequences which may be necessary for the initiation of transcription. The presence of a promoter region is, therefrom sufficient to cause the expression of an operably linked gene sequence.

Operably Linked. As used herein, the term "operably linked" means that the promoter controls the initiation of expression of the gene. A promoter is operably linked to a sequence of proximal DNA if upon introduction into a host cell the promoter determines the transcription of the proximal DNA sequence or sequences into one or more species of RNA. A promoter is operably linked to a DNA sequence if the promoter is capable of initiating transcription of that DNA sequence.

Prokaryote. The term "prokaryote" is meant to include all organisms without a true nucleus, including bacteria.

Eukaryote. The term "eukaryote" is meant to include organisms and cells which have a true nucleus, including mammalian cells.

Host. The term "host" is meant to include not only prokaryotes, but also eukaryotes such as yeast and filamentous fungi, as well as plant and animal cells. The term includes an organism or cell that is the recipient of a replicable expression vehicle.

Substantially homologous. The term "substantially homologous" as used herein refers to the ability of a first DNA sequence encoding Bcl-Y to hybridize to a second DNA sequence encoding the foregoing, under stringent conditions, for example, at about 0.1x sodium citrate sodium chloride buffer (SSC) at a temperature of about 65° C.

Substantially pure. The term "substantially pure" means that the protein or molecule of interest is essentially free from any other detectable biological constituents.

Functional Equivalent. As used herein, a "functional equivalent" of the Bcl-Y protein is a protein which possesses a biological activity or immunological characteristic substantially similar to a biological activity or immunological characteristic of non-recombinant Bcl-Y. The term "functional equivalent" is intended to include the "fragments," "variants," "analogues," "homologues," or "chemical derivatives" of a molecule which possess the biological activity of the Bcl-Y protein of the invention.

Fragment. A "fragment" of a molecule such as Bcl-Y is meant to refer to any variant of the molecule which possess the biological activity of the Bcl-Y protein.

Variant. A "variant" of a molecule is meant to refer to a molecule substantially similar in structure and biological activity or immunological characteristics to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

Analog. An "analog" of a molecule is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are described, for example, in Remington's Pharmaceutical Sciences (1980). Procedures for coupling such moieties to a molecule are well known in the art.

Anti-Antibody. By the term "anti-antibody" is intended an antibody directed against antigenic determinants on another antibody.

Anti-Idiotypic Antibody. By the term "anti-idiotypic antibody" is intended an antibody directed against an idiotypic determinant of another antibody.

Idiotope. By the term "idiotope" is intended an idiotypic determinant, i.e., an antigenic determinant on a variable domain of an immunoglobulin molecule.

Idiotype. By the term "idiotype" is intended a set of one or more idiotopes that distinguish a clone of immunoglobulin producing cells from other clones. Idiotypes occur in the variable domains of immunoglobulin molecules and may be within, near to, or outside of the antigen binding site; antibodies to idiotypes located within or near the antigen biding site will prevent the immunoglobulin from combining with the antigen.

Idiotype-anti-idiotype Network. By the term "idiotype-anti-idiotype network" is intended a B-cell regulatory mechanism. Activation of a B cell results in a clone of plasma cells producing immunoglobulin of a single idiotype, which, because it was previously present in very small quantities, can be recognized as "nonself" and results in the production of anti-idiotypic antibodies directed against its idiotypic determinants. There can also be anti-anti-idiotypic antibodies directed against the second antibodies, antibodies directed against them, and so forth. These antibodies react with antigen receptors on B cells and T helper and suppressor cells, as well as with circulating antibodies, to enhance or suppress production of the initial antibody by various mechanisms.

Modulate. By the term "modulate" is intended, for the purposes of the present invention, the induction of apoptosis by the administration of the Bcl-Y protein of the invention, an active fragment thereof, a functional equivalent thereof, and/or the suppression or induction of apoptosis by the administration of a Bcl-Y hybrid or Bcl-Y mutant, or the administration of a vector containing cDNA encoding any of the foregoing, to the particular cells of an individual suffering from any degenerative disorder which results in inappropriate cell growth, for example, including lymphomas, genotypic tumors, cancer, or, disorders characterized by inappropriate cell death, for example, including AIDS which results in T-cell death, in order to stabilize inappropriate cell proliferation or inappropriate cell death and preferably to restore normal cell behavior.

Administration. By the term "administration" is intended any mode of administration which results in the delivery of the therapeutic agent across the cell membrane and into the desired cell. The site of administration and cells will be selected by one of ordinary skill in the art based upon an understanding of the particular degenerative disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc., with the requirement that the therapeutic agent cross the cell membrane. The therapeutic agent of the present invention can be the Bcl-Y protein and/or functional equivalents thereof and/or Bcl-Y hybrids or Bcl-Y mutants and/or a vector containing cDNA encoding the foregoing.

Therapeutic Agent. By the term "therapeutic agent" is intended the present Bcl-Y protein, fragments, functional equivalents and/or hybrids or mutants thereof as well as vectors containing cDNA encoding any of the foregoing. The present therapeutic agent can be administered alone or in combination with and/or concurrently with other suitable drugs and/or courses of therapy.

Degenerative Disorder. By the term "degenerative disorder" is intended for purposes of this invention, any disorder characterized by inappropriate cell proliferation or inappropriate cell death or in some cases, both. By the term "inappropriate cell proliferation" is intended a statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells. By the term "inappropriate cell death" is intended a statistically significant decrease in cell number as compared to the presence of that particular cell type in the normal population. Such underrepresentation may be due to a particular degenerative disorder, including, for example, AIDS (HIV), which results in the inappropriate death of T-cells, autoimmune diseases which are characterized by inappropriate cell death. By the term "autoimmune disease" is intended a disorder caused by an immune response directed against self antigens. Such diseases are characterized by the presence of circulating autoantibodies or cell-mediated immunity against autoantigens in conjunctions with inflammatory lesions caused by immunologically competent cells or immune complexes in tissues containing the autoantigens. Such diseases include systemic lupus, erythematosus (SLE), rheumatoid arthritis.

Suppression. By the term "suppression" is intended for the purposes of this invention the result achieved by administering an amount of a therapeutic agent containing Bcl-Y hybrids or Bcl-Y mutants thereof effective to suppress apoptosis in an individual suffering from a degenerative disorder characterized by inappropriate cell death. Suppression of apoptosis is achieved when the numbers of the particular affected cell type remain stable or increase in number to a level within the range observed in the normal cell population. By the term "stable" is intended the state achieved when a statistically significant decrease in cell number is no longer observed in the individual being treated, as compared to the cell number observed at the onset of the course of treatment.

Induction. By the term "induction" is intended for the purposes of this invention the result achieved by the administration of an amount of a therapeutic agent containing the Bcl-Y of the invention effective to induce apoptosis in cells of an individual suffering from a degenerative disorder characterized by inappropriate cell proliferation. The induction of apoptosis is achieved when cell numbers remain stable or decrease to a level within the range observed in the normal cell population. By the term "stable" is intended the state achieved during the course of treatment when a statistically significant increase in cell proliferation is no longer observed as compared to the cell number observed at the onset of the course of treatment. One of ordinary skill in the art can readily determine whether the induction of apoptosis has been achieved.

Bcl-Y Hybrid. By the term "Bcl-Y hybrid" is intended for the purposes of this invention, proteins which are hybrid proteins of the present Bcl-Y proteins, fragments thereof, and/or functional equivalents or mutants thereof, with other apoptosis associated proteins encoded by genes including, for example, Bcl-2, Bax, c-myc, LMW5-HL, Bcl-Y, Bcl-$X_L$, Bcl-$X_S$, BHRF-1, Mcl, A1 and ced9, fragments thereof and/or functional equivalents thereof, in order to produce a protein which exhibits enhanced, decreased, or intermediate apoptosis induction or suppression activity as compared to the activity of Bcl-Y alone. Such hybrids can be produced, for example, by fusing the first half of the coding region of the Bcl-Y cDNA with the second half of the coding region of the cDNA for Bcl-2, or Bax, or Bcl-$X_L$, or Bcl-$X_S$ or vice versa. Additionally, by adding or replacing segments of Bcl-2, Bax, Bcl-$X_L$ or Bcl-$X_S$ to the Bcl-Y cDNA, chimeric gene products of therapeutic value can be generated. One of ordinary skill in the art can readily produce and employ such hybrids using techniques well known in the art. One of ordinary skill in the art can readily determine whether a particular hybrid exhibits enhanced, decreased or intermediate apoptosis induction or suppression activity using known screening methods and as described herein.

Normal Cell Behavior. By the term "normal cell behavior" is intended for the purposes of this invention, cells in which apoptosis proceeds normally. Normal cell behavior is observed in an organism which is able to remove senescent, damaged, or abnormal cells that could interfere with organ function or develop into tumors. Apoptosis which proceeds normally represents a coordinated cellular response to noxious stimuli that are not immediately lethal.

Patient/Individual. By the term "patient" or "individual" is intended for the purposes of the present invention, animals, including humans and mammals, who suffer from a degenerative disorder.

Bcl-Y mutant. By the term "Bcl-Y mutant" is intended for the purposes of the present invention a mutant of Bcl-Y which exhibits the reverse (apoptosis suppression) activity of the Bcl-Y protein of the invention due to the substitution of one or more amino acids or corresponding nucleotides.

Apoptosis associated protein Bcl-Y. By the term "apoptosis associated protein Bcl-Y" is intended for the purposes of the present invention both the isolated naturally occurring and isolated recombinantly produced protein (i.e., synthetic Bcl-Y) which exhibits, inter alia, apoptosis induction from human tissue including, for example, tumor cells and established human cell lines, and from tissues of other animals including meals. This term includes any analog, homolog, mutant or derivative of isolated naturally occurring Bcl-Y including fragments having less than the naturally occurring number of amino acids, such as partial fragments of natural or synthetic Bcl-Y which retain the biological or immunological characteristics of the polypeptide disclosed in this application.

This term also includes any peptide which contains the sequence of an isolated naturally occurring Bcl-Y protein, or analog or homolog thereof, together with one or more flanking amino acids, which retains the biological or immunological characteristics of the Bcl-Y protein of the invention.

The present invention pertains to both the expression of full-length Bcl-Y and of functional derivatives of this protein, including allelic variants of Bcl-Y and species or viral homologs of Bcl-Y. Species homologs can be identified, isolated and recombinantly produced using the present nucleotide probes and procedures as described herein, being methods well known in the art. Further, one of ordinary skill in the art can readily determine whether a particular peptide is a functional equivalent of Bcl-Y using methods well known in the art.

More specifically, this term includes proteins encoded by the nucleotide sequence as shown in FIG. 4, and proteins having the amino acid sequence as shown in FIG. 4, allelic variants, species homologs and viral homologs thereof, as well as functional derivatives thereof including fragments which retain the biological characteristics of the present Bcl-Y, and proteins that are substantially homologous thereto, which retain the biological or immunological characteristics of the Bcl-Y protein of the invention.

Also, this term includes mutant proteins which differ from the present Bcl-Y protein by one or more amino acids or corresponding nucleotides, which difference results in the reversal of function of Bcl-Y, i.e., the mutant protein exhibits apoptosis suppression activity. Accordingly, the present Bcl-Y proteins and the mutant proteins, or their corresponding polynucleotide sequences, are useful for the regulation of apoptosis in cells.

II. Genetic Engineering of Bcl-Y, Functional Equivalents Thereof and Mutants Thereof This invention comprises amino acid sequences of Bcl-Y or Bcl-Y mutant, Genetic sequences coding for such amino acid sequences, expression vehicles containing the Genetic sequences, hosts transformed therewith and recombinant Bcl-Y and antisense RNA produced by such transformed host expression. The invention further comprises antibodies directed against Bcl-Y and/or fragments thereof or against Bcl-Y mutants.

The process for genetically engineering such protein sequences, according to the invention, is facilitated through the cloning of genetic sequences which are capable of encoding the peptide and through the expression of such genetic sequences. As used herein, the term "genetic sequences" is intended to refer to a nucleic acid molecule (preferably DNA). Genetic sequences which are capable of encoding the proteins are derived from a variety of sources. These sources include genomic DNA, cDNA, synthetic DNA, and combinations thereof. The preferred source of the genomic DNA or mRNA is human tissue including heart, lung, tumor cells, brain, placenta, liver, skeletal muscle, kidney and pancreas. The mRNA may then be used to obtain cDNA by techniques known to those skilled in the art. Probes may be synthesized based on the nucleotide sequence of Bcl-Y by methods known in the art.

The Bcl-Y protein or fragment genomic DNA of the invention may or may not include naturally occurring introns. Moreover, such genomic DNA may be obtained in association with the 5' promoter region of the Bcl-Y protein gene sequences and/or with the 3' transcriptional termination region. Further, such genomic DNA may be obtained in association with the genetic sequences which encode the 5' non-translated region of the Bcl-Y protein mRNA and/or with the genetic sequences which encode the 3' non-translated region. To the extent that a host cell can recognize the transcriptional and/or translational regulatory signals associated with the expression of the mRNA and protein, the 5' and/or 3' non-transcribed regions of the native gene, and/or the 5' and/or 3' non-translated regions of the mRNA, may be retained and employed for transcriptional and translational regulation. Bcl-Y protein genomic DNA can be extracted and purified from human tissue by means well known in the art (for example, see *Guide to Molecular Cloning Techniques*, S. L. Berger, et al., eds., Academic Press (1987)).

Alternatively, mRNA can be isolated from any cell which produces or expresses the protein, and used to produce cDNA by means well known in the art (for example, see *Guide to Molecular Cloning Techniques*, S. L. Berger, et al., eds., supra. Preferably, the mRNA preparation used will be enriched in mRNA coding for such Bcl-Y protein, either naturally, by isolation from cells which are producing large amounts of the protein, or in vitro, by techniques commonly used to enrich mRNA preparations of specific sequences, including for example sucrose gradient centrifugation, or PCR. cDNA can then be prepared for example, by reverse transcription. The cDNA can then be amplified by PCR using suitable primers.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding the Bcl-Y protein or its functional equivalents may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, et al., (*In: Molecular Cloning, A Laboratory Manual*, Cold Spring Harbor Laboratories, Cold Spring Harbor, N.Y., 2d. ed. (1989)), and are well known in the art.

Libraries containing the Bcl-Y protein clones may be screened and a Bcl-Y clone identified by any means which specifically selects for Bcl-Y protein DNA such as, for example, (a) by hybridization with an appropriate nucleic acid probe(s) containing a sequence specific for the DNA of this protein, or (b) by hybridization-selected translational analysis in which native mRNA which hybridizes to the clone in question is translated in vitro and the translation products are further characterized, or, (c) if the cloned genetic sequences are themselves capable of expressing mRNA, by immunoprecipitation of a translated Bcl-Y or fragment product produced by the host containing the clone.

Oligonucleotide probes specific for the protein which can be used to identify clones to this protein can be designed from knowledge of the amino acid sequence of the Bcl-Y protein. The sequence of amino acid residues in a peptide is designated herein either through the use of their commonly employed three-letter designations or by their single-letter designations. A listing of these three-letter and one-letter designations may be found in textbooks such as *Biochemistry*, 2ed., Lehninger, A., Worth Publishers, New York, N.Y. (1975). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

Because the genetic code is degenerate, more than one codon may be used to encode a particular amino acid (Watson, J. D., *In: Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: Molecular Biology of the Gene, 3rd Ed., W. A. Benjamin, Inc., Menlo Park, Calif. (1977)), one or more different oligonucleotides can be identified from the amino acid sequence, each of which would be capable of encoding the present Bcl-Y or fragment protein. The probability that a particular oligonucleotide will, in fact, constitute the actual protein coding sequence can be estimated by considering abnormal base pairing relationships and the frequency with which a particular codon is actually used (to encode a particular amino acid) in eukaryotic cells. Such "codon usage rules" are disclosed by Lathe, et al., J. Molec. Biol. 183:1–12 (1985). Using the "codon usage rules" of Lathe, a single oligonucleotide sequence, or a set of oligonucleotide sequences, that contains a theoretical "most probable" nucleotide sequence capable of encoding the Bcl-Y protein sequences is identified.

The suitable oligonucleotide, or set of oligonucleotides, which is capable of encoding a fragment of the Bcl-Y protein gene (or which is complementary to such an oligonucleotide, or set of oligonucleotides) may be synthesized by means well known in the art (see, for example, Synthesis and Application of DNA and RNA, S. A. Narang, ed., 1987, Academic Press, San Diego, Calif.) and employed as a probe to identify and isolate the cloned Bcl-Y protein gene by techniques known in the art. Techniques of nucleic acid hybridization and clone identification are disclosed by Maniatis, et al. (In: Molecular Cloning, A Laboratory Manual, Cold Spring Harbor Laboratories, Cold Spring Harbor, N.Y. (1982)); Berger, et al., (In: Guide to Molecular Cloning Techniques, Academic Press (1988)); Sambrook, et al., (In: Molecular Cloning, A Laboratory Manual, Cold Spring Harbor Press, Cold Spring Harbor, N.Y., 2d ed. (1989); and by Hames, et al. (In: Nucleic Acid Hybridization, A Practical Approach, IRL Press, Washington, D.C. (1985)), which references are herein incorporated by reference. Those members of the above-described gene library which are found to be capable of such hybridization are then analyzed to determine the extent and nature of the Bcl-Y protein encoding sequences which they contain.

To facilitate the detection of the desired Bcl-Y or fragment protein DNA encoding sequence, the above-described DNA probe is labeled with a detectable group or label. Such detectable Group or label can be any material having a detectable physical or chemical property. Such materials have been well-developed in the field of nucleic acid hybridization and in General most any label useful in such methods can be applied to the present invention. Particularly useful are radioactive labels, such as $^{32}$P, $^{3}$H, $^{14}$C, $^{35}$S, $^{125}$I, or the like. Any radioactive label may be employed which provides for an adequate signal and has a sufficient half-life. The oligonucleotide may be radioactively labeled, for example, by "nick-translation" by well-known means, as described in, for example, Rigby, et al., J. Mol. Biol. 113:237 (1977) and by T4 DNA polymerase replacement synthesis as described in, for example, Deen, et al., Anal. Biochem. 135:456 (1983).

Alternatively, polynucleotides are also useful as nucleic acid hybridization probes when labeled with a non-radioactive marker such as biotin, an enzyme or a fluorescent or chemiluminescent group. See, for example, Leary, et al., Proc. Natl. Acad. Sci, USA 80:4045 (1983); Renz, et al., Nucl. Acids Res. 12:3435 (1984); and Renz, M., EMBO J. 6:817 (1983).

Thus, the actual identification of the Bcl-Y protein sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the Bcl-Y protein gene.

In an alternative way of cloning the Bcl-Y protein gene, a library is prepared using an expression vector, by cloning DNA or, more preferably, cDNA prepared from a cell capable of expressing the Bcl-Y protein, into an expression vector. The library is then screened for members which express the Bcl-Y protein, for example, by screening the library with antibodies to the Bcl-Y protein.

The above discussed methods are, therefore, capable of identifying genetic sequences which are capable of encoding Bcl-Y proteins or fragments thereof. In order to further characterize such genetic sequences, and, in order to produce the recombinant protein, it is desirable to express the proteins which these sequences encode. Such expression identifies those clones which express proteins possessing characteristics of the Bcl-Y proteins. Such characteristics may include the ability to specifically bind antibody to the Bcl-Y protein and the ability to elicit the production of an antibody or antibodies which are capable of binding to the Bcl-Y protein.

III. Expression of Bcl-Y protein, Fragments Thereof, Functional Equivalents Thereof, and Mutants Thereof To express the Bcl-Y protein or a functional equivalent, or mutant thereof, transcriptional and translational signals recognizable by an appropriate host are necessary. The cloned Bcl-Y encoding sequences, obtained, for example, through the methods described above, and preferably in a double-stranded form, may be operably linked to sequences controlling transcriptional expression in an expression vector, and introduced into a host cell, either prokaryotic or eukaryotic, to produce recombinant Bcl-Y protein or a functional equivalent thereof. Depending upon which strand of the Bcl-Y encoding sequence is operably linked to the sequences controlling transcriptional expression, it is also possible to express Bcl-Y antisense RNA or a functional equivalent thereof.

Expression of Bcl-Y in different hosts may result in different post-translational modifications which may alter the properties of the Bcl-Y. The present invention encompasses the expression of the Bcl-Y protein, or functional equivalent thereof, or Bcl-Y mutant, in prokaryotic or eukaryotic cells, and particularly, eukaryotic expression is preferred.

Preferred prokaryotic hosts include bacteria such as *E. coli*, Bacillus, Streptomyces, Pseudomonas, Salmonella, Serratia, etc. The most preferred prokaryotic host is *E. coli*. Other enterobacteria such as *Salmonella typhimurium* or *Serratia marcescens*, and various *Pseudomonas species* may also be utilized. Under such conditions, the protein may not be glycosylated. The procaryotic host must be compatible with the replicon and control sequences in the expression plasmid.

To express the Bcl-Y protein (or a functional equivalent thereof) or Bcl-Y mutant in a prokaryotic cell (such as, for example, *E. coli*, *B. subtilis*, Pseudomonas, Streptomyces, etc.), it is necessary to operably link the Bcl-Y encoding sequence to a functional prokaryotic promoter. Such promoters may be either constitutive or, more preferably, regulatable (i.e., inducible or derepressible). Examples of constitutive promoters include the int promoter of bacteriophage lambda, the bla promoter of the Beta-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of *E. coli*, the alpha-amylase (Ulmanen, I., et al., *J. Bacteriol*. 162:176–182 (1985)) and the sigma-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the gene-encoding sequence. Such ribosome binding sites are disclosed, for example, by Gold, L., et al. (*Ann. Rev. Microbiol.* 35:365–404 (1981)).

Especially preferred eukaryotic hosts include mammalian cells either in vivo, in animals or in tissue culture.

Expression of the Bcl-Y in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, et al., *J. Mol. Appl. Gen.* 1:273–288 (1982)); the TK promoter of Herpes virus (McKnight, S., *Cell* 31:355–365 (1982)); the SV40 early promoter (Benoist, et al. *Nature (London)* 290:304–310 (1981)); in yeast, the yeast gal4 gene promoter (Johnston, et al. *Proc. Natl. Acad. Sci. USA* 79:6971–6975 (1982); Silver, et al., *Proc. Natl. Acad. Sci. USA* 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes the Bcl-Y protein, or a functional equivalent thereof, does not contain any intervening codons which are capable of encoding a methionine. The presence of such codons results either in the formation of a fusion protein (if the AUG codon is in the same reading frame as the Bcl-Y encoding DNA sequence) or a frame-shift mutation (if the AUG codon is not in the same reading frame as the Bcl-Y encoding sequence).

If desired, a fusion product of the Bcl-Y may be constructed. For example, the sequence coding for the Bcl-Y or fragment thereof may be liked to a signal sequence which will allow secretion of the protein from or the compartmentalization of the protein in, a particular host. Such signal sequences may be designed with or without specific protease sites such that the signal peptide sequence is amenable to subsequent removal.

Transcriptional initiation regulatory signals can be selected which allow for repression or activation, so that expression of the operably linked genes can be modulated. Of interest are regulatory signals which are temperature-sensitive, such that by varying the temperature, expression can be repressed or initiated, or which are subject to chemical regulation, e.g., by a metabolite. Also of interest are constructs wherein the Bcl-YmRNA and antisense RNA are provided in a transcribable form, but with different promoters or other transcriptional regulatory elements such that induction of Bcl-Y mRNA expression is accompanied by repression of antisense RNA expression, and/or repression of Bcl-YmRNA expression is accompanied by induction of antisense RNA expression.

Translational signals are not necessary when it is desired to express Bcl-Y antisense RNA sequences.

If desired, the non-transcribed and/or non-translated regions 3' to the sequence coding for the Bcl-Y protein can be obtained by the above-described cloning methods. The 3'-non-transcribed region may be retained for its transcriptional termination regulatory sequence elements; the 3'-non-translated region may be retained for its translation termination regulatory sequence elements, or for those elements which direct polyadenylation in eukaryotic cells. Where the native expression control sequence signals do not function satisfactorily in the host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the Bcl-Y DNA construct into the host cell chromosomal DNA, or to allow it to exist in an extrachromosomal form.

If the Bcl-Y DNA encoding sequence and an operably linked promoter are introduced into a recipient eukaryotic cell as a non-replicating DNA (or RNA) molecule, which may either be a linear molecule or a closed covalent circular molecule which is incapable of autonomous replication, then the expression of the Bcl-Y protein may occur through the transient expression of the introduced sequence.

Genetically stable transformants may be constructed with vector systems, or transformation systems, whereby Bcl-Y DNA is integrated into the host chromosome. Such integration may occur de novo within the cell or, in a preferred embodiment, be assisted by transformation with a vector which functionally inserts itself into the host chromosome, for example, with retroviral vectors, transposons or other DNA elements which promote integration of DNA sequences into chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., pp. 445–470 (1981); Broach, J. R., *Cell* 28:203–204 (1982); Bollon, et al., *J. Clin, Hematol. Oncol.* 10:39–48 (1980); Maniatis, T., In: *Cell Biology: A Comprehensive Treatise,* Vol. 3, "Gene Expression," Academic Pres, NY, pp. 563–608 (1980)), and are commercially available. For example, mammalian expression vector systems which utilize the MSV-LTR promoter to drive expression of the cloned gene, and in which it is possible to contransfect with a helper virus to amplify plasmid copy number, and integrate the plasmid into the chromosomes of host cells, have been described (Perkins, et al., *Mol. Cell Biol.* 3:1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of the Bcl-Y protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like.

Bcl-Y can be purified by growing the transformed host cells under suitable conditions which are well known in the art, the cells can be harvested and disrupted to extract total cellular protein. The protein can then, for example, be placed on a sizing column such as sepharose or agarose beads, and proteins of the correct molecular weight can be collected. The predicted molecular weight of Bcl-Y is 23.4 kD and it runs with an apparent molecular weight of approximately 26 kD on SDS polyacrylamide gels.

Further purification can be effected by use of an anti-Bcl-Y antibody. Such an antibody can be used to immunoprecipitate Bcl-Y proteins from the set of cellular proteins of the correct approximate molecular weight. Such antibodies can, for example, be raised against polypeptides synthesized according to the sequence or subsequences of the sequence shown in FIG. 4. Alternatively, the antibodies can be raised against fusion proteins, which contain Bcl-Y sequences as well as those of other proteins. After immunoprecipitation, the Bcl-Y proteins can be released from the antibodies to provide a substantially pure preparation of Bcl-Y protein.

The Bcl-Y DNA coding sequences, of the present invention may be used to obtain Bcl-Y antisense RNA genetic sequences, inasmuch as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of a Bcl-Y antisense RNA in the transformed cell. Antisense RNA and its expression may be used to interact with an endogenous Bcl-Y DNA or RNA in a manner which inhibits or represses transcription or translation of the Bcl-Y genes in a highly specific manner. Use of antisense RNA probes to block gene expression is described, for example, in Lichtenstein, C., *Nature* 333:801–802 (1988).

IV. Construction and Identification of Antibodies Raised Against Bcl-Y, Functional Equivalents, Fragments, Hybrids, or Mutants Thereof In the following description, reference will be made to various methodologies well-known to those skilled in the art of immunology. Standard reference works setting forth the general principles of immunology include the work of Catty, D., (*Antibodies, A Practical Approach,* Vol. 1, IRL Press, Washington, D.C. (1988)); Klein, J., (*Immunology: The Science of Cell-Noncell Discrimination,* John Wiley & Sons, New York (1982)); Kennett, et al., (*Monoclonal Antibodies, Hybridoma: A New Dimension in Biological Analyses,* Plenum Press, New York (1980)); Campbell, A. ("Monoclonal Antibody Technology," In: *Laboratory Techniques in Biochemistry and Molecular Biology,* Vol. 13 (Burdon, R., et al., eds.), Elsevier, Amsterdam (1984)); and Eisen, H. N. (*In: Microbiology,* 3rd ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab)$_2$ fragments) which are capable of binding an antigen. Fab and F(ab)$_2$ fragments lack the Fc fragment of intact antibody, clear more rapidly from the circulation, and may have less non-specific tissue binding of an intact antibody (Wahl, et al., *J. Nucl. Med.* 24:16–325 (1983)).

The antibodies of the present invention have specificity to one or more epitopes present on the Bcl-Y peptide, or an idiotype on the present Bcl-Y. The antibodies of the invention can be polyclonal or monoclonal, provided that they are made with the present Bcl-Y polypeptide or fragment thereof as the immunogen. Both of these types of antibodies can be utilized in the applications described herein.

The present antibodies can be used to detect the presence of the present Bcl-Y protein in a human tissue sample. The present Bcl-Y protein can be detected by contacting the sample with an imaging-effective amount of the present detectably labeled appropriate antibody and detecting the label, thereby establishing the presence of the Bcl-Y protein in the sample. Detection can be carried out by imaging in vivo. The Bcl-Y protein can also be detected by known immunoassay techniques, including, for example, RIA, ELISA, etc., using appropriate antibodies according to the invention.

The antibodies of the present invention are prepared by any of a variety of known methods. For example, cells expressing the Bcl-Y protein can be administered to an animal in order to induce the production of serum containing polyclonal antibodies that are capable of binding the Bcl-Y protein. For example, the Bcl-Y protein or fragment thereof is chemically synthesized and purified by HPLC to render it substantially free of contaminants. Such a preparation is then introduced into an animal in order to produce polyclonal antisera of high specific activity.

Polyclonal antibodies can be generated in any suitable animal including, for example, mice, rabbits or goats. The Bcl-Y immunogenic peptide or fragment thereof can be injected by itself or linked to appropriate immunoactivating carriers, such as Keyhole's limpet hemocyanin (KLH). See *Antibodies, A Practical Handbook*, Vols. I and II, D. Catty, ed., IRL Press, Washington, D.C. (1988).

Monoclonal antibodies can be prepared in various ways using techniques well understood by those having ordinary skill in the art. For example, monoclonal antibodies can be prepared using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., In: *Monoclonal Antibodies and T-Cell Hybridomas*, Elsevier, N.Y., pp. 563–681 (1981)); *Monoclonal Antibodies-Hybridomas: A New Dimension in Biological Analysis*, edited by Roger H. Kennett, et al., published by Plenum Press (1980). In general, such procedures involve immunizing an animal with the present Bcl-Y protein, or a fragment thereof. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, et al., *Gastroenterology* 80:225–232 (1981). The hybridoma cells obtained through such a selection are then assayed to identify clones which secrete antibodies capable of binding the Bcl-Y protein.

Through application of the above-described methods, additional cell lines capable of producing antibodies which recognize epitopes of the present Bcl-Y protein can be obtained.

For example, additional hybridomas which produce monoclonal antibodies which enable the detection of the present Bcl-Y protein can be easily produced and isolated with minimal screening. Hybridomas producing monoclonal antibodies specific for epitopes which are found on the present Bcl-Y protein are most effectively produced by first immunizing an animal from which hybridomas can be produced such as, for example, a Balb/c mouse, with initial subcutaneous injections of Freund's adjuvant, followed by booster injections within a few days. The fusion can be carried out using any of the techniques commonly known to those of ordinary skill in the art. The screening of the hybridomas to determine which ones are producing monoclonal antibodies specific for the present peptide is straightforward and can be accomplished in a standard ELISA or RIA format. For example, in an RIA screening format the culture supernatant, or ascites fluid from a hybridoma producing monoclonal antibody is reacted with $^{125}$I-peptide. The isolation of other hybridomas secreting mAbs of the same specificity as those described herein can be accomplished by the technique of anti-idiotypic screening. Potocmjak, et al., *Science* 215:1637 (1982). Briefly, an anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb raised against the present Bcl-Y protein or fragment thereof to which an anti-Id is being prepared. The immunized animal will recognize and respond to the idiotypic determinants of the immunizing antibody by producing an antibody to these idiotypic determinants (the anti-Id antibody).

By using an anti-Id antibody which is specific for idiotypic determinants on a given mAb, it is then possible to identify other B cell or hybridoma clones sharing that idiotype. Idiotypic identity between the antibody product of two clones makes it highly probable that the antibody products of the two clones recognize the same antigenic epitopes.

The anti-Id antibody may also be used as an "immunogen" to induce an immune response in yet another animal, producing a so-called anti-anti-Id antibody. The anti-anti-Id may be epitopically identical to the original mAb which induced the anti-Id.

Thus, by using antibodies to the idiotypic determinants of a mAb, it is possible to identify other clones expressing antibodies of identical specificity.

Accordingly, mAbs generated against the present Bcl-Y protein may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for the antigen epitope. The anti-Id mAbs thus have their own idiotypic epitopes, or "idiotopes" structurally similar to the epitope being evaluated.

For replication, the hybridoma cells of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Of special interest to the present invention are antibodies which are produced in humans, or are "humanized" (i.e., non-immunogenic in a human) by recombinant or other technology such that they will not be antigenic in humans, or will be maintained in the circulating serum of a recipient for a longer period of time.

Humanized antibodies may be produced, for example by replacing an immunogenic portion of an antibody with a corresponding, but non-immunogenic portion (i.e., chimeric antibodies) (Robinson, et al., International Patent Publication PCT/US86/02269; Akira, et al., European Patent Application 184,187; Taniguchi, M., European Patent Application 171,496; Morrison, et al., European Patent Application 173,494; Neuberger, et al., PCT Application WO 86/01533, Cabilly, et al., European Patent Application 125,023; Better, et al., Science 240:1041–1043 (1988); Liu, et al., Proc. Natl. Acad. Sci. USA 84:3439–3443 (1987); Liu, et al., J. Immunol. 139:3521–3526 (1987); Sun, et al., Proc. Natl. Acad. Sci. USA 84:214–218 (1987); Nishimura, et al., Canc. Res. 47:999–1005 (1987); Wood, et al., Nature 314:446–449 (1985)); Shaw, et al., J. Natl. Cancer Inst. 80:1553–1559 (1988). General reviews of "humanized" chimeric antibodies are provided by Morrison, S. L. (Science, 229:1202–1207 (1985)) and by Oi, et al., BioTechniques 4:214 (1986)).

Suitable "humanized" antibodies can be alternatively produced as described by Jones, et al., Nature 321:552–525 (1986); Verhoeyan, et al., Science 234:1534 (1988), and Beidler, et al., J. Immunol. 141:4053–4060 (1988).

The present Bcl-Y protein, fragments thereof, hybrids thereof, Bcl-Y mutants, or antibodies thereto can be utilized in immunoassays for the detection of the Bcl-Y protein in a human tissue sample. For example, antibodies against the present Bcl-Y protein can be used to detect the present Bcl-Y protein in a human tissue sample. The immunoassays can be competitive or sandwich, as is otherwise well known and they all depend on the formation of antibody-antigen immune complex. These assays are well known to those of skill in the art.

For purposes of the assays, the antibody or antigen can be immobilized or labeled. There are many carriers to which the antibody/antigen can be bound for immobilization and which can be used in the present invention. Well-known carriers include but are not limited to glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the antibody or antigen, or will be able to ascertain such, using routine experimentation.

Depending on the particular embodiment of the invention, one or more of the antibodies or antigen(s) peptide(s) will be coupled with a detectable label such as an enzyme, radioactive isotope, fluorescent compound, chemiluminescent compound, or bioluminescent compound.

Those of ordinary skill in the art will know of other suitable labels for binding to the antibodies or antigen(s) peptide(s) or will be able to ascertain such using routine experimentation. Furthermore, the binding of these labels to the antibodies or antigen(s) can be done using standard techniques commonly known to those of ordinary skill in the art.

The antibodies or antigen peptide(s) can be bound to an enzyme. This enzyme, in turn, when later exposed to its substrate will react with the substrate in such a manner as to produce a chemical moiety which can be detected, as, for example, by spectrophotometric or fluorometric means. Examples of enzymes that can be used to detectably label are amylate dehydrogenase, staphylococcal nuclease, delta-5-steroidisomerase, yeast alcoholdehydrogenase, alphaglycerophosphate dehydrogenase, triose phosphate isomerase, alkaline phosphatase, asparaginase, glucose oxidase, betagalactosidase, ribonuclease, urease, catalase, glucose-6-phosphate dehydrogenase, glucoamylase, and acetylcholinesterase.

The presence of an antibody or antigen can also be detected by labeling the antibody or antigen with a radioactive isotope. The presence of the radioactive isotope can be determined by such means as the use of a gamma counter or a scintillation counter. Isotopes which are particularly useful are $^3$H, $^{125}$I, $^{32}$P, $^{35}$S, $^{14}$C, $^{51}$Cr, $^{36}$Cl, $^{57}$Co, $^{59}$Fe, $^{75}$Se, and $^{152}$Eu.

It is possible to detect the presence of the antibody or antigen by labeling the antibody or antigen peptide with a fluorescent compound. When the fluorescently labeled antibody or antigen peptide is exposed to light of the proper wavelength, its presence can then be detected due to fluorescence of the dye. Among the most common fluorescent labeling compounds are fluorescein isothiocyanate, rhodamine, phycoerythrin, phycocyanin, allophycocyanin, o-phthaldehyde, and fluorescamine.

Another way in which the antibody or antigen can be detectably labeled is by coupling it to a chemiluminescent compound. The presence of the chemiluminescent-tagged antibody or antigen peptide is then determined by detecting the presence of luminescence that arises during the course of a chemical reaction. Examples of particularly useful chemiluminescent labeling compounds are luminol, isoluminol, aromatic-acridinium ester, imidaxole, acridinium salt, and oxalate ester.

Likewise, a bioluminescent compound may also be used to label the antibody or antigen peptide. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies or antigen peptide(s) for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably labeled third antibody in lyophilized form or in solution. Such a kit can be used for sandwich assays.

In addition, the carrier means may also contain a plurality of containers each of which comprises different, predetermined amounts of the present Bcl-Y peptide. These latter containers can then be used to prepare a standard curve into which can be used to interpolate the results obtained from the sample containing the unknown amount of the present Bcl-Y protein.

Imaging can be carried out in vitro or in vivo. In vitro imaging can be done with the labels mentioned previously. In vivo imaging is done with diagnostically effective labeled antibodies. The term "diagnostically effective" means that the amount of detectably labeled antibody administered is sufficient to enable detection of the site of Bcl-Y protein presence when compared to a background signal.

Generally, the dosage of detectably-labeled antibody or antigen(s) for diagnosis will vary depending on considerations such as age, condition, sex, and extent of disease in the patient, counterindications, if any, and other variables, to be adjusted by the individual physician. Dosage can vary from 0.01 mg/kg to 2,000 mg/kg, preferably 0.1 mg/kg to 1,000 mg/kg.

The term "diagnostically labeled" means that the antibody has attached to it a diagnostically detectable label.

There are many different imaging labels and methods of labeling known to those of ordinary skill in the art. Examples of the types of labels which can be used in the present invention include radioactive isotopes and paramagnetic isotopes.

For diagnostic in vivo imaging, the type of detection instrument available is a major factor in selecting a given radionuclide. The radionucleotide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionucleotide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 ke V range, which may be readily detected by conventional gamma cameras.

For in vivo diagnosis, radionucleotides may be bound to antibody or antigen either directly or indirectly by using an intermediary functional group. Intermediary functional groups which are often used to bind radioisotopes which exist as metallic ions to antibody or antigen are diethylenetriaminepentaacetic acid (DTPA) and ethlenediaminetetracetic acid (EDTA). Typical examples of metallic ions which can be bound to immunoglobulins are $^{99m}Tc$, $^{123}I$, $^{111}In$, $^{131}I$, $^{97}Ru$, $^{67}Cu$, $^{67}Ga$, $^{72}As$, $^{89}Zr$, and $^{201}Tl$.

The antibodies used in the method of the invention can also be labeled with paramagnetic isotopes for purposes of in vivo diagnosis. Elements which are particularly useful (as in magnetic resonance imaging (MRI) techniques) in this manner include $^{157}Gd$, $^{55}Mm$, $^{162}Dy$, $^{52}Cr$, and $^{56}Fe$.

Preparations of the imaging antibodies for administration include sterile aqueous or non-aqueous solutions, suspensions, and emulsions. Examples of non-aqueous solvents are propyleneglycol, polyethyleneglycol, vegetable oil such as olive oil and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed. Mac Eds. 1980.

Of course, the expressed Bcl-Y protein is an intracellular protein. Accordingly, those of skill will recognize that in vivo diagnostic and therapeutic methods employing the antibodies of the invention may require some mechanism by which such antibodies can detect Bcl-Y in the cell. One such method is to introduce the antibodies or fragments thereof into the cell itself across the cell membrane. This may be accomplished, for example, by attaching the antibody to a ligand for which the target cell contains receptor sites. The antibody can thus be transported into the cell membrane or across the cell membrane along with the ligand. Suitable ligands include growth factors and cytokines that are internalized upon receptor binding. Suitable growth factors include epidermal growth factor (EGF), tumor growth factor alpha (TGF-α), fibroblast growth factor (FGF), insulin, and insulin-like growth factors 1 and 2 (TGF-1 and -2). Suitable cytokines include G-CSF, GM-CSF, erythropoietin, IL-1 and IL-2. It is noted that there are also receptors that carry nutrients and vitamins into cells. These nutrients are suitable for use as ligands in the present invention and include foliate, dihdrofoliate, tetrahydrofoliate and vitamin B12.

The choice of a carrier ligand will depend on several factors, as those of skill will appreciate. These include, for example, the kinetics of the ligand and its receptor, and of overall transport, which may include passive or active, with actively transported ligands preferred. The means of attaching the antibody to the ligand also will vary within limits, and may be, for example, covalent or ionic, bearing in mind that such attachment should not unacceptably alter ligand-receptor affinity.

Examples of receptors suitable for such applications include the receptor for low density lipoprotein (LDL), which has been shown to contain all the information necessary for receptor endocytosis, Davis et al., *J. Cell Biol.* 107(6/3): Abstr. No. 3112 (1988), as well as known brain-specific receptors such as those for dopamine. In this regard, it will be appreciated that the ligand may itself be an antibody or fragment specific for the receptor, to which may be conjugated the antibody of the invention.

Moreover, those of skill may find it particularly desirable to employ antibody fragments of the invention (such as, for example, Fab or F(ab')$_2$ fragments), which are less likely to interfere with the ligand-receptor interaction, and may be more easily transported across the cell membrane. Single-chain antibodies may prove preferable for these and other reasons, as will be appreciated by those of skill.

When an antibody is to be transported into the cell's membrane or into the cell as described above, it will be preferred to diagnostically or therapeutically label the antibody in such a way that the label will be relatively more effective when the antibody is bound to its antigenic site on the Bcl-Y protein. This may be accomplished, for example, by employing a label which becomes active or detectable as a result of formation of the antigen-antibody complex. Alternatively, the antibody itself may be labeled in such a way that antigen-antibody complex formation induces a conformational change in the antibody to expose or more fully expose the previously unexposed or less fully exposed label. All of the above criteria, and others, will be apparent to those of skill in carrying out these aspects of the invention.

It is also possible to utilize liposomes having the antibodies of the present invention in their membranes to specifically deliver the antibodies to the target area. These liposomes can be produced so that they contain, in addition to the antibody, such therapeutic agents as drugs, radioisotopes, lectins and toxins, which would act at the target site.

V. Pharmaceutical Compositions

Pharmaceutical compositions containing a therapeutically effective amount of the present Bcl-Y protein, functional equivalents, fragments and/or hybrids and/or mutants thereof, as well as vectors containing cDNA encoding one or more of the foregoing, are useful for treating patients suffering from degenerative disorders characterized by inappropriate cell death or inappropriate cell proliferation.

Hybrids of Bcl-Y include hybrids of Bcl-Y and for example Bcl-2, ced-9, Bcl-X, Bcl-$X_L$, Bcl-$X_S$, Bax, Mcl, c-myc, LMW5-HL, BHRF-1 and A1. Such hybrids exhibit enhanced, decreased or intermediate apoptosis induction or suppression activity as compared to the activity of Bcl-Y alone. These hybrids can be readily selected, produced and employed by one or ordinary skill in the art. Pharmaceutical compositions according to the invention thus will contain a therapeutically effective amount of the present Bcl-Y protein, functional equivalents, fragments and/or hybrids and/or mutants thereof, and may optionally contain one or more pharmaceutically acceptable carriers and/or excipients, known to those of ordinary skill in the art. Administration, dosage and frequency, and length of the course of treatment can be readily optimized for a particular patient by one of ordinary skill in the art. For example, the present pharmaceutical composition can be formulated as sterile aqueous or non-aqueous suspensions or emulsions, as described above in Section IV, for example for solutions for intravenous administration.

VI. Therapeutic Applications

Programmed cell death is a process in which cells undergo nuclear condensation and fragmentation during normal development of healthy tissues and organs. The process is essential in maintaining the balance between growth of new cells and elimination of old cells. When apoptosis does not work properly, either by causing cells to die prematurely or by preventing them from dying when scheduled, various disorders develop.

The present apoptosis associated Bcl-Y protein, functional equivalents, fragments and/or hybrids and/or mutants thereof as well as vectors containing cDNA encoding the foregoing are useful for treating degenerative disorders, which disorders are characterized by inappropriate cell death or inappropriate cell proliferation. Particular disorders may involve different cell types whereby it may be desirable to induce apoptosis in one cell type while suppressing apoptosis in the other. For example, it may be desirable to suppress apoptosis in lung tissue cells in a patient suffering from acute lung injury by administering the Bcl-Y mutant protein of the invention (or by effecting expression of such Bcl-Y mutant protein in those cells) while inducing apoptosis in fibroblast cells which may be present in the lung due to the inflammatory response by administering the Bcl-Y protein of the invention (or by effecting Bcl-Y protein expression in those cells).

The therapeutic agents of the present invention can be administered as discussed above with the requirement that the agent must cross the cell membrane. The therapeutic agent can be administered alone, in combination with or during the course of treatment with other acceptable therapies known in the art for treating a particular disorder. For example, the present therapeutic agents can be administered to induce apoptosis in a cancer patient who is also undergoing classic cancer therapy including, for example, radiation therapy, chemotherapy, and treatment with anti-cancer drugs including, for example, topoisomerase inhibitors, alkylating agents, antimetabolites, and hormone antagonists. Further, the present therapeutic agents can also be administered concurrently with gene therapy. For example, the present therapeutic agents can be administered to a patient suffering from a degenerative disorder of the central nervous system while the patient is concurrently undergoing gene therapy to replenish neutrophic hormones.

Premature widespread apoptosis (inappropriate cell death) causes much of the damage associated with degenerative disorders including, for example, AIDs, chemotherapy and radiation, and tissue atrophy. In AIDs patients, lymphocytes are activated even in the asymptomatic phase of the HIV infection, and those cells die prematurely by apoptosis. Such disorders may admit of treatment by administration of a Bcl-Y mutant protein.

Those of skill will appreciate that administration of the various proteins of the invention to particular target cells or tissues, as described herein, is intended to comprehend the administration of the proteins themselves as well as the expression by the target cells or tissues of the nucleotide sequences encoding those proteins by various known means and in accordance with the teachings of the present specification.

Degenerative disorders characterized in inappropriate cell proliferation include cancer, autoimmune disorders, tissue hypertrophy, and inflammatory disorders including inflammation arising from acute tissue injury including, for example, acute lung injury. These disorders can be treated by administering the present Bcl-Y protein or functional equivalent.

Cancers arise when changes in DNA cause the anomalous accumulation of cells. The comparative rates of cell division and cell deaths determine how fast a cancer grows. Some cancer cells divide more slowly than normal cells, but the cancer may still expand because of prolonged cell life span. Apoptosis is an efficient method for preventing malignant transformation because it removes cells with genetic lesions. Defective apoptosis can promote cancer development, both by allowing accumulation of dividing cells and by obstructing removal of genetic variants with enhanced malignant potential. The present therapeutic agents, including the present Bcl-Y protein, functional equivalents, fragments, and hybrids thereof along with vectors containing cDNA encoding the one or more of the foregoing, can be administered to cancer patients to induce apoptosis.

Many types of cancer can be treated by the administration of the present therapeutic agents, including for example, carcinomas, sarcomas, and leukemia/lymphomas, including for example, carcinomas such as adenocarcinomas, squamous carcinomas, carcinoma of the organs including breast, colon, head, neck, etc.; sarcomas including chondrosarcoma, melanosarcoma, etc.; and leukemia and lymphomas including acute lymphomatic leukemia, acute myelogenous leukemia, non-Hodgkin's lymphoma, Burkitt's lymphoma, B-cell lymphomas, T-cell lymphomas, etc. Other conditions amenable to treatment using the present therapeutic agent include fungal infections.

The present therapeutic agents can be used to treat autoimmune diseases. Random gene recombination and somatic hypermutation can potentially generate autoreactive T and B lymphocytes throughout life. Under normal conditions immature lymphocytes that bind autoantigens die by apoptosis. However, a defect in the deletion of these lymphocytes predisposes one to autoimmunity.

The present therapeutic agents can be administered to patients suffering from autoimmune disorders to induce apoptosis in autoreactive T lymphocytes, for example, in patients suffering systemic lupus erythematosus. Other autoimmune diseases amenable to treatment by suppressing or inducing apoptosis through the administration of the present therapeutic agents include, for example, rheumatoid arthritis, myasthenia gravis, Grave's disease, Hashimoto's thyroiditis, insulin-resistent diabetes, allergic rhinitis, asthma, functional autonomic abnormalities, juvenile insulin-dependent diabetes, Addison's disease, idiopathic hypoparathyroidism, spontaneous infertility, premature ovarian failure, pemphigus, Bullous pemphigoid, primary biliary cirrhosis, autoimmune hemolytic anemia, idiopathic thrombocytopenic purpura, idiopathic neutropenia, Goodpasture's syndrome, rheumatoid arthritis and Sjogren's syndrome.

The present therapeutic agents can be used to treat inflammation resulting from acute lung injury, by inducing apoptosis. The disease process begins with an explosive inflammatory response in the alveolar wall. In the aftermath of the resulting tissue destruction, extensive fibroproliferation of the alveolar air space ensues, consisting of fibroblasts, capillaries and their connective tissue products. Fukuda, Y., et al., *Am. J. Pathol.* 126:171–182 (1987). An important mechanism for the systematic elimination of the foregoing is apoptosis, i.e., programed cell death.

The present therapeutic agents can also be used to treat degenerative disorders due to premature or excessive cell loss during aging which can lead to organ disfunction and disease. Such degenerative disorders include degenerative diseases of the central nervous system due to aging or other factors which result in the death of neurons. The present therapeutic agents containing Bcl-Y mutant protein or hybrids thereof can be administered to a patient suffering from such a degenerative disorder to suppress apoptosis. Further, the present therapeutic agents can be administered concurrently with gene therapy to provide genes encoding neutrophic hormones including, for example, nerve growth factor. Other conditions amenable to treatment utilizing the present therapeutic agents include, for example, Alzheimer's disease.

One of ordinary skill in the art can readily identify other degenerative disorders characterized by inappropriate cell death or inappropriate cell proliferation or both which are amenable to treatment using the present therapeutic agents. The present therapeutic agents can include the Bcl-Y protein itself, as well as fragments, functional equivalents and/or hybrids and/or mutants thereof, which are administered to a target cell. Alternatively, therapeutic agents according to the invention can be administered by infecting the target cell with a vector containing cDNA encoding one or more of the foregoing. The present therapeutic agents can be administered to the desired target cell as discussed below, for example, by choosing a receptor on the target cell surface which is specific for that cell type. The present therapeutic agents can be administered alone or in combination with other acceptable drug therapies. Further, the present therapeutic agents can be administered concurrently with other acceptable therapies specific for the particular degenerative disorder being treated. For example, the present therapeutic agents can be administered concurrently with chemotherapeutic agents, gene therapy, or the like. Whether it is the Bcl-Y protein itself or the a vector encoding the protein, the therapeutic agent must cross the cell membrane.

One method for introducing the Bcl-Y protein or fragments thereof into the cell's membrane or into the cell itself is by attaching the protein to a ligand for which the target cell contains receptor sites. The protein can thus be transported into the cell membrane or across the cell membrane along with the ligand.

The choice of a carrier ligand will depend on several factors, as discussed herein and known to those of skill. Suitable tissue-specific receptors include: Brain: nerve growth factor receptor (NGF-R); breast: prolactin receptor; stomach: gastrin receptor; skin: melanocyte stimulating hormone receptor (MSH-R), liver: asialoglycoprotein receptor; thyroid: thyroid stimulating hormone receptor (TSH-R); ovaries: luteinizing hormone receptor (LH-R), testis: human chorionic gonadotrophin receptor (hCG-R), T-cells: T-cell receptors; B cells: CD19; lung hyaluronate receptor CD44 isoform 4V (J. Cell. Biol. 124, 7182, 1994). In this regard, it will be appreciated that the ligand may be an antibody or fragment specific for the receptor, to which may be conjugated the Bcl-Y protein of the invention.

It may be desirable to employ active Bcl-Y fragments according to the invention which are less likely to interfere with the ligand-receptor interaction, and which may be more easily transported across the cell membrane.

When a protein is to be transported across the cell's membrane or into the cell as described above and the ligand is an antibody, it will be preferred to diagnostically or therapeutically label the protein in such a way that the label will be relatively more effective when the protein is bound, such as, for example, by means analogous to those described herein in the context of antibody transport.

It is also possible to utilize liposomes having the proteins of the present invention in their membrane to specifically deliver the present Bcl-Y proteins to the target area. These liposomes can be produced so that they contain, in addition to the Bcl-Y protein, such other therapeutic agents including drugs, radioisotopes, lectins and toxins, which would be released at the target site.

A preferred manner for administering the Bcl-Y encoding nucleotide sequences (and their functional equivalents and/or hybrids and/or mutants) for diagnostic or therapeutic purposes is by the use of viral vectors. Suitable viral vectors for gene transfer include retroviruses (reviewed in Miller, et al., *Methods Enzymol.* vol. 217, p.581–599 (1993)) including human immunodeficiency virus (HIV), adenovirus derivatives (for examples see Erzurum, et al. *Nucleic Acids Res.* Vol. 21, p.1607–12 (1993); Zabner, et al., *Nat. Genet.* Vol. 6, p.75–83 (1994); Davidson, et al., *Nat. Genet.* vol. 3, p.219–223 (1993)) adeno-associated virus (AAV), (i.e. see Flotte, et al., *Proc. Natl. Acad. Sci.* vol. 90, p.10613–7 (1993)) and Herpes virus vectors (i.e. see Anderson, et al., *Cell Mol. Neurobiol.* vol. 13, p.503–15 (1993)). Other suitable viruses can be readily selected and employed by those of ordinary skill in the art. Other methods for DNA delivery include liposome mediated gene transfer (Alton, et al., *Nat. Genet.* vol. 5, p. 135–42 (1993); Nabel, et al., *Proc. Natl. Acad. Sci USA* vol. 90, p. 11307–11 (1993)).

The use of viral vectors for introduction of genes into mammalian cells is also reviewed, for example, in Varmus, *Science* 240(4858):1427 (1988); Eglitis et al., *BioTechniques* 6,7:608 (1988); Jaenisch, *Science* 240(4858):1468 (1988); and Bernstein et al., *Genet. Eng.* (N.Y.) 7:235 (1985).

For the purposes of the present invention, it may be preferred to employ an attenuated viral or retroviral strain. Thus, for example, it is possible to use as vectors for the DNA sequences of the invention retroviruses having attenuated cytopathicity, such as HIV-2$_{ST}$ (Kong et al., *Science* 240(4858):1525 (1988)) or HIV-2$_{UC1}$ (Evans et al., *Science* 240(4858):1523 (1988)), which enter neural cells by a CD4-dependent mechanism (Funke et al., *J. Exp. Med.* 165:1230 (1987)). The neurobiology of HIV infections is described, for example, in Johnson et al., *FASEB J.* 2(14):2970 (1988). Those of skill will be able to target different cell populations having known susceptibilities to viruses by the exercise of routine skill. For example, CD4 is known to have a variant transcript in the human brain, with its highest content in forebrain (Maddon et al., *Cell* 47:333 (1986). Possible methods to target retroviral gene expression to specific cell types are reviewed by Boris-Lawrie and H. Temin Curr. Opin. Genet. Dev. vol. 3, p.102–9 (1993).

Ideally, then, the choice of a gene delivery system will be made by those of skill, keeping in mind the objectives of efficient and stable gene transfer, with an appropriate level of gene expression, in a tissue-appropriate manner, and without any adverse effects. See, for example, Wolff et al., *Rheum. Dis. Clin. North Am.* 14(2):459 (1988). With respect to delivery to a central nervous system target, many viral vectors, including HIV, offer the advantage of being able to cross the blood-brain barrier (Johnson et al., *FASEB J.* 2(14):2970 (1988)).

VII. Diagnostic Applications

Antibodies raised against the present Bcl-Y protein, fragments, functional equivalents, or hybrids or mutants thereof can be used to detect the Bcl-Y protein in a human tissue sample, as well as to diagnose degenerative disorders associated with the expression of the Bcl-Y protein. Further, such antibodies can also be used to monitor the progress of degenerative disorders associated with the expression of the Bcl-Y protein.

Any source of human cells is suitable for use in the diagnostic testing in the present invention. The cells can be isolated from any human tissue including for example, heart, lung, tumor cells, brain, placenta, liver, skeletal muscle, kidney and pancreas. Extraction of proteins from the cell sample may be performed by any of the many means known in the art. For example, cells may be lysed by a detergent by mechanical means. If desired, nucleic acids can be removed from the cell preparation by enzymatic digestion or by precipitation with agents such as streptomycin. Such means are well known in the art.

Antibodies can be generated which are immunoreactive with the Bcl-Y proteins by the methods set forth herein. Appropriate antibodies can then be screened using the natural gene products of Bcl-Y.

The extracted proteins from the cell sample may be contacted with the antibody under suitable conditions for antibody-antigen complex formation. Generally, such conditions are physiological conditions. The protein extract may be bound to a solid support such a nitrocellular filter or a microtiter plate.

The antibody will generally bear a label which is a radio label, a florescent label, or an enzyme conjugate which under appropriate conditions produces, for example, a colored reaction product. Antibodies and antibody labeling are described herein and known to those of skill. Alternatively, if the antibody is not labeled, it can be detected by means of a second antibody from another species which is reacted with the first antibody. Suitable assay techniques, labels and means of detection are discussed herein.

A parallel sample to the test sample is employed to provide the control. The control sample consists of an equivalent amount of proteins extracted from cells, preferably in the same manner as those of the test sample. The amount of protein can readily be determined by employing techniques well known in the art, including, for example, the Lowry or Bradford techniques. The cells used for preparing the control sample may be selected from cells of the same cell type as the test cells, isolated from a normal human not suffering from the degenerative disorder from which the human from which the test sample was taken suffers, cells of the same cell type as the test sample isolated from an established normal cell line, and cells from the human who is being tested, which cell type is different from the cell type of the test cells.

Test samples can also be screened for elevated levels of mRNA transcribed from the Bcl-Y gene, according to methods well known in the art. For example, RNA extracted from B-cells may be used, or alternatively mRNA may be isolated from total cellular RNA. The mRNA may be purified, for example, by affinity chromatography on oligo (dT cellulose) which binds to the poly (A) tract at the 3' end of most mRNA. As is well known to those skilled in the art, it is essential that ribonuclease activity be minimized during preparation and assaying.

A DNA probe may be selected from any of the protein coding sequences of the Bcl-Y gene. Preferably, the probe will be selected from sequences of the 5' or 1st exon of the gene, so that all three species of RNA can be detected. Preferably, the probe contains at least 15 nucleotides of the Bcl-Y sequence. In order to perform the hybridization, it is desirable that the probe be single stranded. Thus, if the probe is double stranded, it should be denatured to a single stranded form. Means for denaturing are well known in the art, including alkali or heat treatment. The probe can then be contacted with the RNA derived from the cell sample under conditions where homologous RNA-DNA hybrids form and are stable. Such conditions are well known in the art. Means for detecting hybrids are many and well known, but often involve the use of radiolabeled probes and nucleases which degrade single stranded DNA. Other methods known in the art may be used.

Control samples can be derived from any of these cell sources described above for use in the antibody diagnostic tests. Samples and controls should preferably be prepared in parallel under similar conditions.

The diagnostic methods and compositions of the present invention are useful for determining whether a disease/degenerative disorder is linked to abnormal Bcl-Y expression, as well as for determining the effect of over expression or loss of expression of Bcl-Y in animal models such as transgenic mice and/or homozygous null mice. Methods for determining whether a disease/degenerative disorder is linked to abnormal Bcl-Y expression include analyzing Bcl-Y expression in diseased tissue as compared to normal tissue by for example, Northern and/or Western blots, as well as by other assay methods readily chosen and employed by those of ordinary skill in the art. Once it has been determined that a disease/degenerative disorder is linked to abnormal Bcl-Y expression, the disease/disorder can be diagnosed in an individual.

The following Examples are offered by way of illustration, not by way of limitation.

EXAMPLES

Example 1

A. Materials and Methods

1. Degenerate PCR. Poly A+ RNA was prepared from total cellular RNA by oligo dT chromatography using the PolyATract system (Promega) following the manufacturers protocol. Approximately 0.5 µg of poly A+ RNA was converted to cDNA using the Gibco/BRL (MD) cDNA synthesis pre-amplification system. The reverse transcription reactions were primed with random hexamer oligonucleotides. Two degenerate oligonucleotide primers were synthesized with the following sequences:
BD2: 5'-CGGAAGATCTAA(C,T)TGGGG(N)(A,C)G(N)(A,G)T(N)GT-3' [SEQ ID NO:1]
BU3: 5'-GCTTCTGCAG(A,G)AA(N)(C,G)C(N)TCCCA(N)CC(N)CC-3' [SEQ ID NO:2]

PCR reactions contained the following components: approximately 100 ng of cDNA template, 12 µM of each primer (BD2 and BU3), 1.5 mM MgCl2, 0.2 mM dNTP, 50 mM KCl, 10 mM Tris-HCL [pH 8.3], and 2.5 units Taq polymerase (Perkin Elmer) in a total volume of 50 µl. The reaction was denatured at 94° for 5 minutes followed by two amplification cycles at low annealing temperature consisting of: 94° 1 min., 40° 1 min., and 72° 1 min. Thirty additional cycles were subsequently performed at normal annealing temperature: 94° 1 min., 55° 1 min., 72° 0.5 min. The PCR reactions were precipitated with ethanol, resuspended and digested with Bgl II and Pst I which cut at the ends of primers BD2 and BU3, respectively. The digested PCR products were then electrophoresed on a 9% polyacrylamide Tris-borate-EDTA gel. DNA fragments of the expected size (around 200 bp) were excised and purified by electrophoretic transfer to NA45 membranes (Schleicher and Schluell). The purified DNA was cloned into pBluescript KS (Stratagene), and individual clones were analyzed by DNA sequencing using the Sequenase system (US Biochemicals).

2. Isolation of cDNA clones. The 200 bp Bcl-Y partial cDNA fragment was 32-P labeled by the random hexamer priming method to a specific activity $>10^8$ cpm/µg. This probe was then used to screen a Lamda ZAP II (Stratagene) Jurkat cDNA library. Positive phage were plaque purified by secondary and tertiary screening, and cDNA inserts in positive lamda clones were rescued as plasmids by in vivo phagemid excision following the protocol supplied by Stratagene. Clones were further analyzed by restriction enzyme site mapping and DNA sequencing. A portion of the cDNA sequence extending 5' of the Bcl-Y open reading frame was isolated by the amplification of cDNA ends PCR method (Frohman, M. A., et al., *Proc. Natl. Acad. Sci. USA* 85:8998–9002 (1988)), using the 5'-Amplifinder RACE system (Clontech).

3. In vitro translation. 35-S labeled proteins were synthesized in vitro using the TnT T7/T3 coupled reticulocyte lysate system (Promega), following the manufacturer's procedures.

4. Western blot analysis. COS7 and NIH3T3 cells were cultured in DMEM supplemented with 10% fetal calf serum, and L-glutamine. Cells were transfected with plasmid DNAs (typically 2 to 8 µg) using Lipofectamine (Gibco/BRL), and cell lysates were prepared 48 hours after transfection. Portions of the cell extracts (approximately 100 µg) were electrophoresed on SDS polyacrylamide gels, and transferred to nylon membranes by standard methods (Harlow, E., et al., *Antibodies: A Laboratory Manual* (1988)). Blots were incubated with the anti-HA epitope monoclonal antibody 12CA5 (Kolodziej, P. A., et al., *Meth. Enzymol.* 194:508–519 (1991)), which was subsequently detected with a secondary antibody using the ECL system (Amersham).

5. Plasmid constructions. All DNA manipulations were performed following standard protocols (Sambrook, J., et al., *Molecular Cloning: A Laboratory Manual* (1989)). The Bcl-Y coding sequence was amplified by PCR using synthetic oligonucleotide primers which introduce BamHi and EcoRI sites at the 5' and 3' end, respectively, of the Bcl-Y reading frame. The DNA sequence of the primers is as follows: 5'-GCAGGATCCGCTTCGGGGCAAGGC-CCAG-3' [SEQ ID NO:3] and 5'-GCGGAATTCGAGTC-ATGATTTGAAGAATC-3' [SEQ ID NO:4]. The Bcl-Y PCR product was digested with BamHI and EcoRI and cloned into the BamHi/EcoRI sites of a pcDNA1/amp derivative (Krek, W., et al., *Science* 262:1557–1560 (1993)) containing a short sequence coding for the hemagglutinin epitope. The correct DNA sequence of the Bcl-Y PCR product was confirmed by DNA sequencing. The resulting construct contains amino acids 2 to 211 of Bcl-Y fused, in frame, to the HA tag encoding peptide sequence: MAYPY-DVPDYASLGS [SEQ ID NO:5]. The HA-Bcl-Y protein is expressed from the CMV enhancer/promoter sequences provided by the pcDNA-1/amp backbone vector (Invitrogen).

Bax and Bcl-X coding sequences were isolated by PCR amplification of Namalwa cell cDNA using primers based on the published cDNA sequences (Boise, L. H., et al., *Cell* 74:597–608 (1993); Oltvai, Z. N., et al., *Cell* 74:609–619 (1993)). The PCR products were initially cloned into pBluescript and sequenced to confirm that the clones contained the wild type Bax and Bcl-X DNA sequences. HA epitope tagged forms of Bax and Bcl-X were generated by subcloning into the pcDNA1/amp derivative described above. A human Bcl-2 cDNA cloned into pBluescript was obtained from Dr. Gerard Evan (ICRF, London).

6. Northern blot analysis. PolyA+ RNA from multiple tumor cell lines was prepared using the FastTrack mRNA isolation system (Invitrogen) following the manufacturer's protocol. Northern blot analysis was performed by standard methods (Sambrook, J., et al., *Molecular Cloning: A Laboratory Manual* (1989)). The tumor cell line Northern blots were hybridized to a 32-P labeled probe derived from the 200 bp Bcl-Y PCR product. A human multiple tissue Northern blot was purchased from Clontech laboratories and hybridized sequentially to 32-P labeled probes encompassing the entire coding regions of Bcl-Y, Bcl-2 and Bax, and β-actin following the supplier's protocol.

7. IL-3 deprivation. IL-3 deprivation studies were performed essentially as described (Hockenbery, D., et al., *Nature* 348:334–336 (1990)). Briefly, cells were cultured for 24 hr in the presence of IL-3, washed extensively, and seeded in 24 well plates at $5 \times 10^5$ cells/ml in media lacking IL-3. Viability was determined by counting live and dead cells after trypan blue staining.

Recombinant retroviruses carrying HA-Bcl-y and HA-Bax were generated by cloning the relevant cDNAs into the pBabe Puro vector (J. P. Morgenstern, H. Land, *Nucl. Acids Res.* 18, 3587–3596 (1990)) and transfecting the WE packaging cell line. Supernatants from the resulting producer cell lines were used to infect FL5.12 cells, and infected cells were selected in media containing 1 μg/ml puromycin.

8. In vitro protein interactions. Glutathione S-transferase fusion proteins of bcl-2 (GST-bcl-2) and its homolog bcl-xl (GST- bcl-xl) were expressed in *E. coli* and purified by affinity chromatography using glutathione-agarose (Smith, D. B. and Johnson, K. S., *Gene* 67, 31 (1988). 35S-Methionine-labeled HA-bcl-y was expressed in vitro using a coupled transcription/translation system in rabbit reticulocyte lysates (Promega). Labeled HA-bcl-y (1–10 nM) was precleared with 10% glutathione-agarose in 10 mM HEPES buffer, pH7.2 containing 0.25% NP-40, 142.5 mM KCl, 5 mM MgCl2 and 1 mM EGTA (Buffer A). GST fusion proteins were added (final concentration 1–3 mM) and the mixtures incubated at 37° C. for 5 min., followed by 60 min. at 4° C. Protein complexes were captured with 10% glutathione-agarose and washed twice with Buffer A and twice with Buffer A without NP-40. Proteins were eluted from the beads by incubation in SDS-PAGE sample buffer at 100° C. for 5 min and loaded onto 4–20% SDS-polyacrylamide gels. Following electrophoresis, gels were fixed and incubated in a fluorography enhancing solution. (Amplify; Amersham). The gels were dried and subjected to autoradiography at −70° C.

B. Results

1. Cloning of a partial Bcl-Y cDNA by degenerate PCR.

It was anticipated that additional, as yet undiscovered, Bcl-2 family members would likely contain amino acid segments closely resembling domains I and II. The identification and cloning of novel Bcl-2 relatives by PCR using primers based on these homologous domains, was attempted. A series of oligonucleotide primers were synthesized with sequences corresponding to variations of the most conserved amino acids present in domains I and II. The primers contained appropriate DNA sequence degeneracies so that all possible triplet codons for a given amino acid residue were encoded. One particular set of degenerate primers, BD2 and BU3 (see FIG. 1A), were designed to anneal to any cDNA(s) coding for the domain I and II segments NWGR(I,V,M)V, and GGW(E,D)(A,G)F, respectively. Restriction enzyme sites (BglII or PstI) were incorporated into the 5' ends of the primers to facilitate cloning of PCR products.

The human B-cell lymphoma cell line, Namalwa, was initially chosen as a source of cDNA for PCR experiments. It was expected that these cells would express Bcl-2, thereby providing a positive control to ensure that the degenerate primers were capable of amplifying Bcl-2 related cDNA(s). RNA (poly A+) was prepared from Namalwa cells, and converted to cDNA by reverse transcription. The cDNA was then used as template DNA in a PCR reaction containing oligonucleotides BD2 and BU3. Two cycles with low annealing temperature (40 deg.) were performed to permit a small degree of mismatching between the primers and template to increase the effective degeneracy of the primers. This was followed by 30 amplification cycles at a 55 degree annealing temperature. The PCR reactions were digested with BglII and PstI, and electrophoresed on a 9% acrylamide gel. Since the spacing between domains I and II is well conserved (FIG. 1A), the PCR products in the expected size range (around 200 bp) were purified and cloned into a plasmid vector for DNA sequence analysis.

The DNA sequence of eighteen independent clones was determined. Three of the clones were cDNAs clearly unrelated to Bcl-2 and were amplified due to fortuitous homology to the degenerate primers. The majority of the PCR clones, however, appeared to be bona fide Bcl-2 related cDNAs. One isolate each of Bcl-2 and Bcl-$X_L$ was obtained and seven clones were identical to Bax. Six of the clones appeared to be a novel Bcl-2 related gene, which was designated "Bcl-Y" since it was isolated by virtue of its homology to Bcl-2. The conceptual translation of the Bcl-Y cDNA segment cloned by PCR indicates that it is an authentic Bcl-2 relative (FIG. 1B). An open reading frame was maintained between the two PCR primers in the appropriate register, and several key amino acids flanking domains I and II that are also highly conserved among known Bcl-2 family members (Williams, G. T., *Cell* 74:777–779 (1993)), were present at the identical positions in the Bcl-Y sequence (FIG. 1B).

The PCR cloning procedure was repeated with cDNA prepared from the human leukemia cell line U937. In this experiment, two of eighteen PCR clones isolated were Bcl-Y. Subsequent PCR experiments with cDNA from breast, colon and ovarian carcinoma cell lines also yielded substantial numbers of Bcl-Y clones. Thus, Bcl-Y partial cDNA clones could be readily isolated from diverse human tumor cell lines by this method.

2. Expression of Bcl-Y in human tumor cell lines.

Northern blot analysis was performed in order to determine the size of the Bcl-Y mRNA and to examine its range of expression in human tumor cells. The partial Bcl-Y cDNA cloned by PCR was labeled with 32P and used as a probe in Northern blots containing poly A+ RNA from a number of different tumor cell lines. The probe hybridized to a 2.2 kb RNA species in all cell lines examined (FIG. 2), including Namalwa, U937, Jurkat (T-cell, data not shown), several breast carcinoma cell lines (MCF7, BT549, MBAMD468), the colon carcinoma cell lines HT29 and SW116, and the ovarian carcinoma cell line OVCAR3. These results demonstrate that the 2.2 kb Bcl-Y mRNA is expressed in a wide variety of human tumor cell lines.

3. Isolation of a full length Bcl-Y cDNA.

Figure 3:
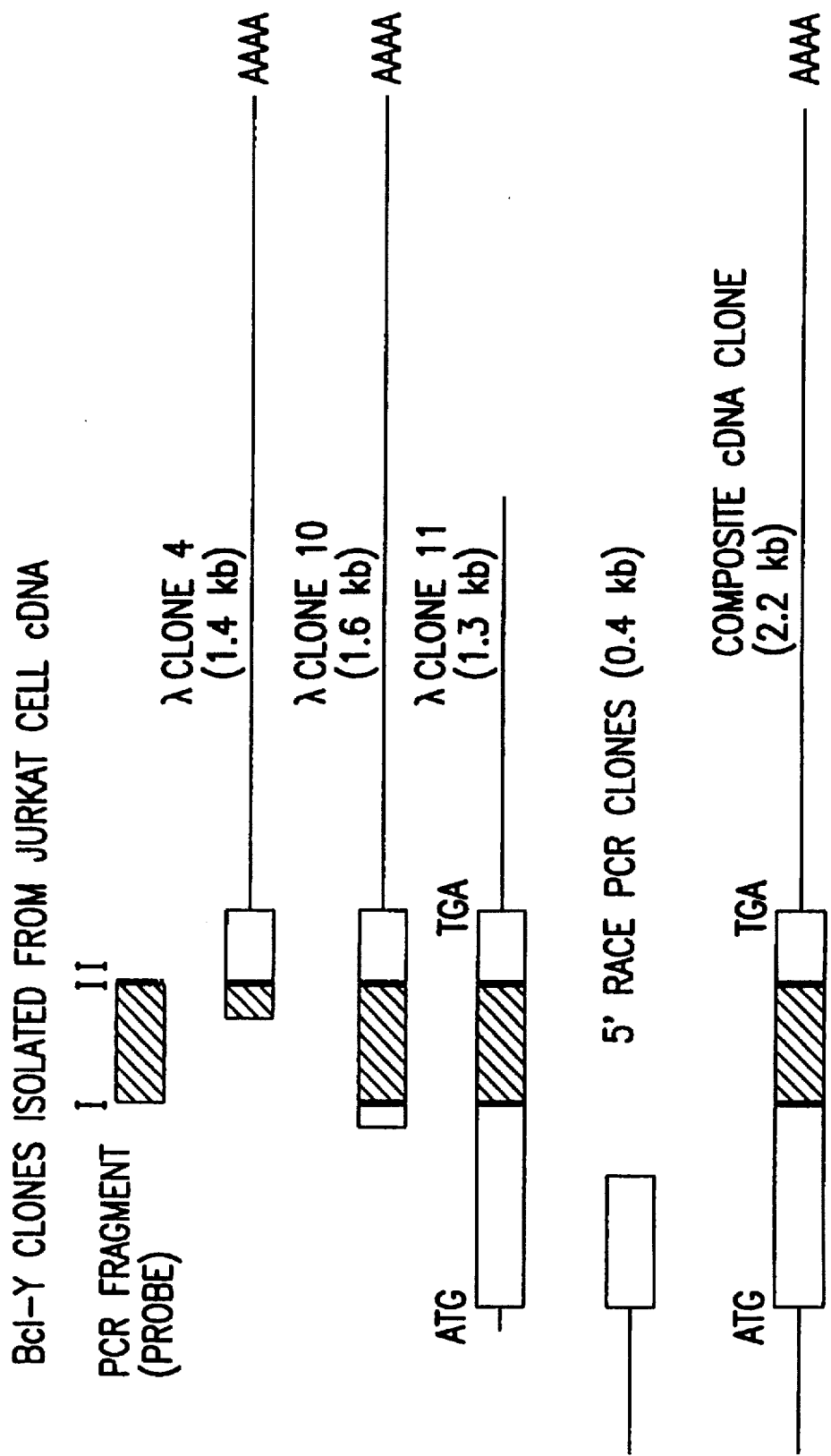
FIG. 3. Bcl-Y clones isolated from Jurkat cell cDNA. A lambda cDNA library was screened with a probe derived from the Bcl-Y PCR product (hatched box, top) and three clones were obtained (clones 4, 10, 11). Lamda clone 11 encompasses the entire Bcl-Y open reading frame (open and hatched box). Additional 5' sequence was obtained by PCR using the 5' RACE method. A composite Bcl-Y cDNA, derived from these overlapping clones, is shown at the bottom.

The cDNA clone isolated by degenerate PCR represented a partial segment (~200 bp) of the predicted 2.2 kb full length Bcl-Y cDNA based on the size of the mRNA on Northern blots. In order to isolate cDNA clone(s) encoding the entire Bcl-Y protein, a Jurkat cell cDNA lambda phage library was screened using the PCR-derived partial cDNA clone as a probe. Three overlapping cDNA clones were obtained that together span about 2.0 kb of the predicted 2.2 kb Bcl-Y full-length cDNA (lambda clones 4, 10, 11, FIG. 3). DNA sequence analysis indicated that lambda clone 11 encompassed the entire Bcl-Y open reading frame (FIG. 3). Additional 5' non-coding sequence (about 200 bp) was cloned by the rapid amplification of cDNA ends (RACE) PCR method. The size of the composite cDNA assembled from these various overlapping clones is approximately 2.2 kb indicating most, if not all, of the Bcl-Y cDNA has been isolated.

The composite cDNA sequence derived from the various overlapping clones, and the conceptual translation of the Bcl-Y open reading frame, is shown in FIG. 4. A methionine codon (ATG), located near the 5' end is predicted to function as the initiating methione since it is preceded by translational stop codons (in all three reading frames), and resembles the consensus initiation sequences described by Kozak (Kozak, M. *Nucl. Acids Res.* 15:8125–8132 (1986)).

4. Bcl-Y is homologous to Bcl-2 family members.

The complete Bcl-Y amino acid sequence was compared to the peptide sequence database (Feb. 10, 1994 release)

using the BLAST network service provided by the NCBI. Bcl-Y showed the highest degree of homology to the human Bcl-2 protein. Bcl-Y exhibited 43% identity to the human Bcl-2 protein over a 54 amino acid section (residues 82 to 136) encompassing domain I (FIG. 5). An 20 amino acid stretch containing domain II (residues 164 to 184), and a 20 residue segment near the N-terminus (residues 54 to 73) showed 40% and 45% identity, respectively, to Bcl-2 alpha (FIG. 5).

Alignment of the deduced Bcl-Y amino acid sequence with the known family of Bcl-2 related proteins is shown in FIG. 6. The highest degree of homology is centered around domains I and II, as is the case with the known Bcl-2 relatives (FIG. 6). Certain amino acids outside of these domains are highly conserved between the previously identified Bcl-2 homologues (Williams, G. T., *Cell* 65:1097–1098 (1991)). These same residues are also present in the Bcl-Y sequence at analogous positions (indicated by the shaded residues, FIG. 6). An additional feature generally shared by Bcl-2 family members is the presence of a C-terminal hydrophobic amino acid domain that provides membrane localization function (underlined residues, FIG. 6). Bcl-Y also contains a similar stretch of hydrophobic residues at its C-terminus. In addition, the hydrophobic stretch ends in each case with one or more basic residues (bold letters, FIG. 6). The location and extent of primary sequence homology, as well as additional structural similarities (MW and the presence of a C-terminal membrane localization sequence) indicates that Bcl-Y is an authentic novel member of the Bcl-2 family.

5. Expression of the Bcl-Y protein in vitro and in transfected cells.

Figure 7A:
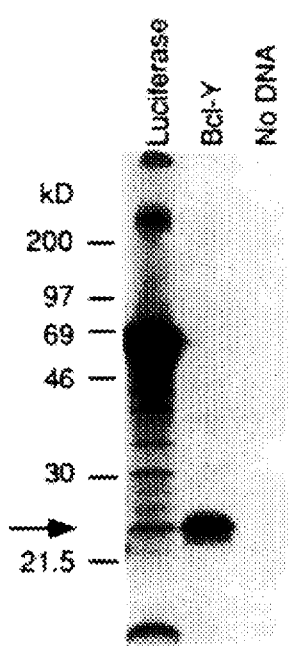
FIG. 7(A). In vitro translation of 35-S labeled Bcl-Y in rabbit reticulocyte lysate. Luciferase was used as a positive control for the translation reactions; "no DNA" indicates a reaction performed with no DNA template. Proteins were resolved by SDS gel electrophoresis and visualized by autoradiography. The gel mobilities of pre-stained protein molecular weight markers (Amersham) are shown.

The deduced amino acid sequence of Bcl-Y predicts a protein of MW 23.4 kD. In vitro translation of lambda clone 11 in rabbit reticulocyte lysates produces a protein with electrophoretic migration on SDS polyacrylamide gels corresponding to a MW of about 26 kd (FIG. 7A), in approximate agreement with the size predicted from conceptual translation of the cDNA sequence.

Figure 7B:
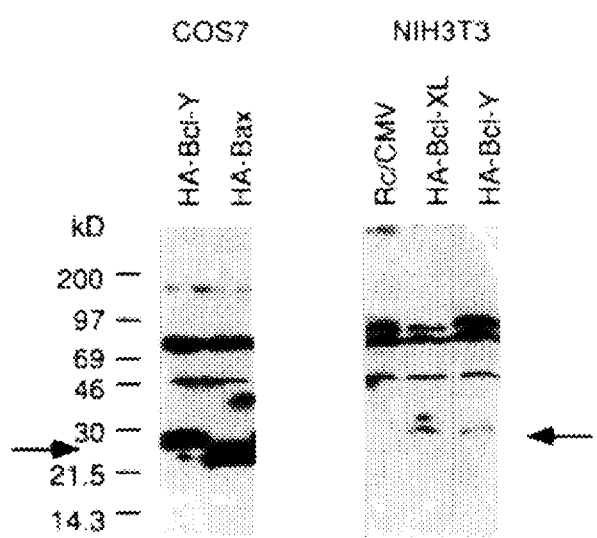
FIG. 7(B). Expression of Bcl-Y in transfected cells. Plasmids expressing the indicated hemagglutinin (HA) epitope-tagged proteins were transfected into either COS7 or NIH3T3 cells. The expression vector Rc/CMV was transfected as a negative control. Proteins were detected 48 hrs after transfection by Western blot of cell lysates with the anti-HA monoclonal antibody 12CA5 (Boehringer Mannheim).

The Bcl-Y protein could also be expressed in transiently transfected cells. In order to detect the protein, the Bcl-Y open reading frame was fused at the amino terminus to a 9 amino acid segment derived from the influenza hemaglutinen antigen (HA). This short peptide provides a well characterized epitope that permits immunological detection of the "tagged" protein by the monoclonal antibody 12CA5 (Kolodziej, P. A., et al., *Meth. Enzymol.* 194:508–519 (1991)). The HA-tagged Bcl-Y open reading frame was cloned into a CMV based eukaryotic expression vector, and transfected into COS7 and NIH3T3 cells. Cell lysates were prepared 48 hrs after transfection, and analyzed by Western blot with the anti-HA monoclonal antibody. The HA-tagged Bcl-Y protein, of the appropriate size, was detected in both the COS7 and NIH3T3 cell extracts (FIG. 7B). These results demonstrate that the protein encoded by the isolated Bcl-Y cDNA can be expressed both in vitro and in vivo.

6. Expression of Bcl-Y in human tissues.

Figure 8:
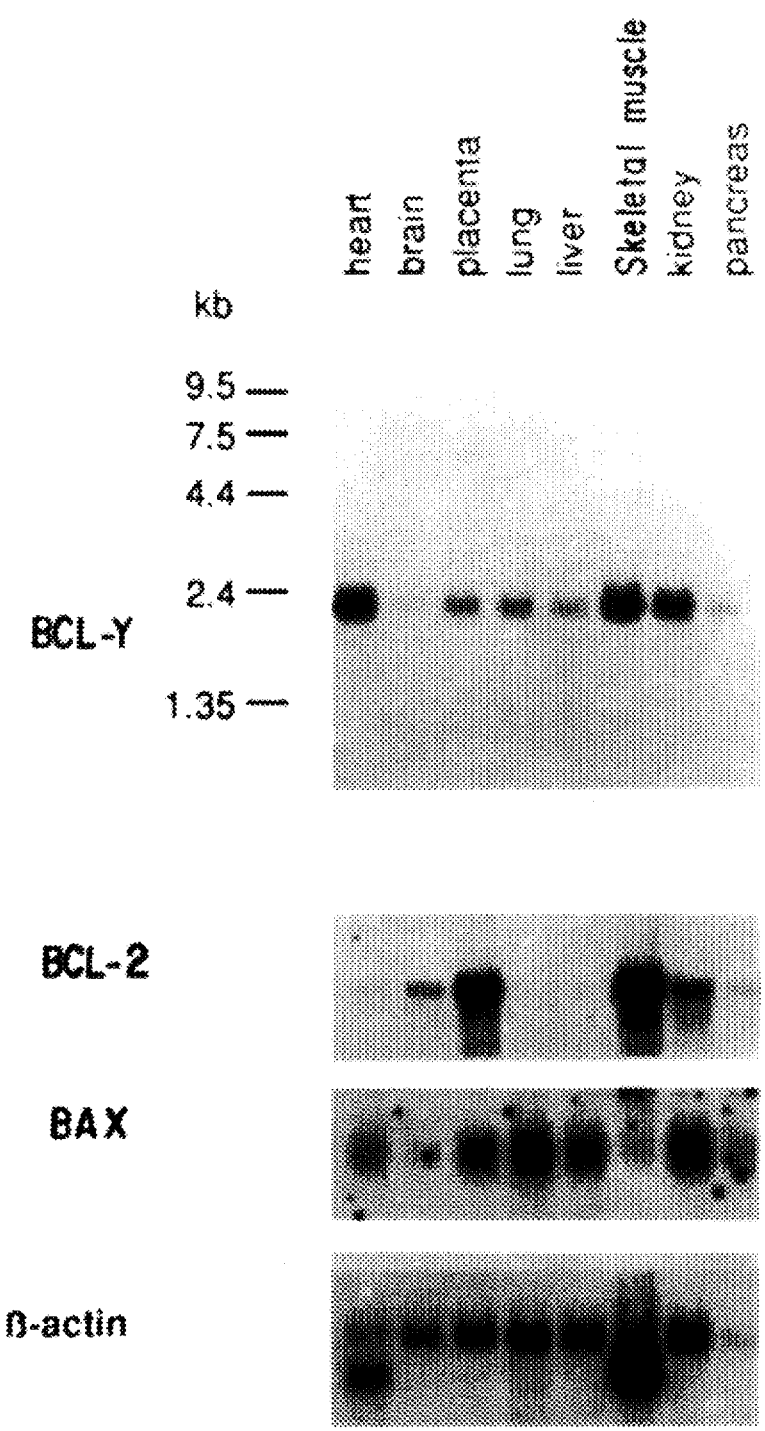
FIG. 8. Expression of Bcl-Y in human tissues. A human multiple tissue northern blot was hybridized sequentially with 32-P labeled probes derived from Bcl-Y, Bcl-2, Bax and β-actin cDNA sequences.

To determine the normal tissue distribution of Bcl-Y gene expression, a northern blot containing RNA from eight different human tissues was hybridized to a probe encompassing the entire Bcl-Y open reading frame. A single 2.2 kb Bcl-Y mRNA was detected in all tissues examined (FIG. 8), suggesting that alternatively spliced Bcl-Y messages, if any, must be present at much lower levels. Heart tissue was found to express the highest levels of Bcl-Y message (when normalized to the levels of β-actin). The northern blot was sequentially re-hybridized to probes for Bcl-2 and Bax (also shown in FIG. 8). These results demonstrate that Bcl-Y has a pattern of expression distinct from these known Bcl-2 family members and its ubiquitous expression indicates that Bcl-Y regulates apoptosis in a broad range of tissues.

7. Expression of Bcl-Y accelerates apotosis in transfected cells.

Figure 9A:
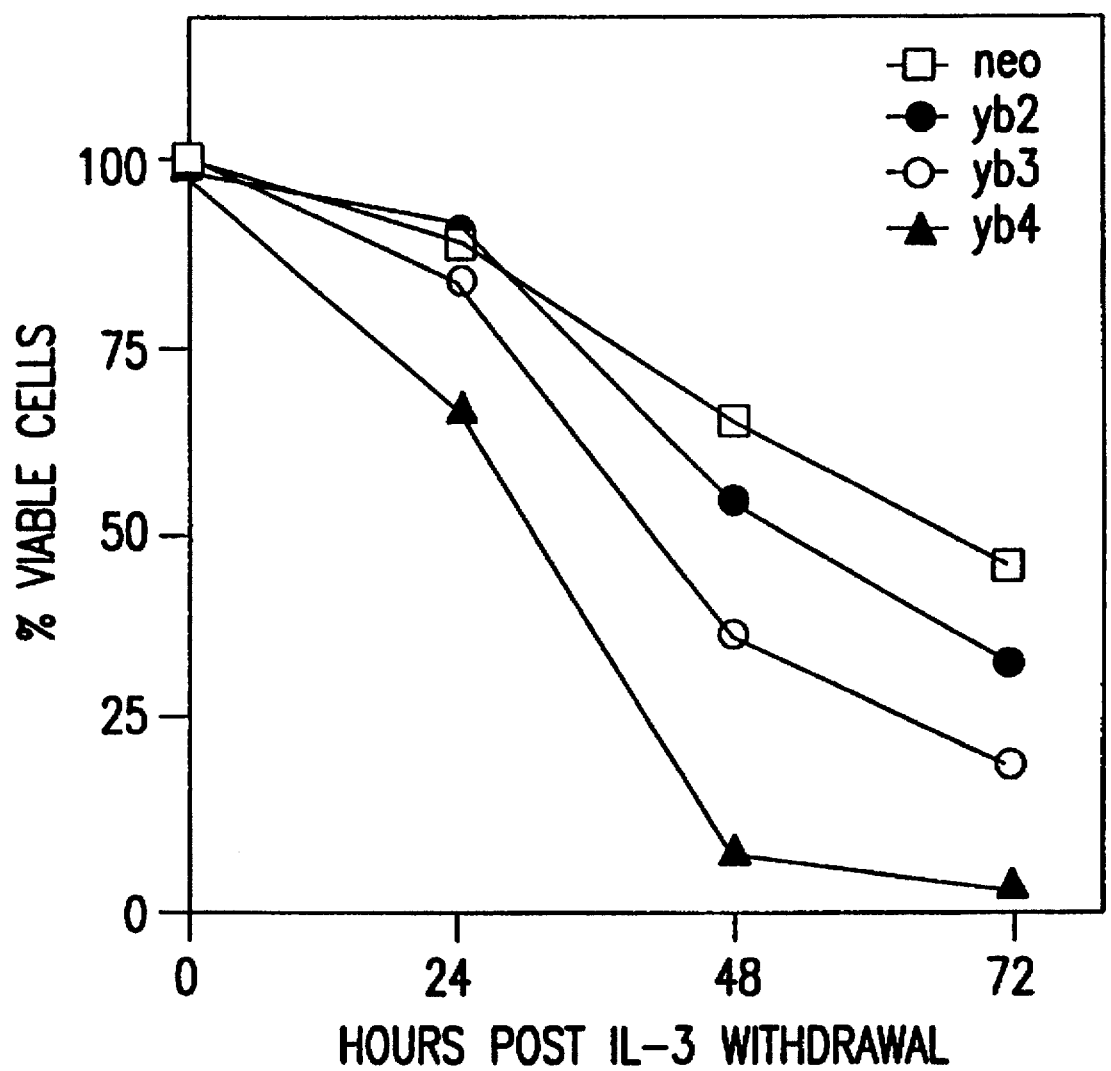
FIG. 9(A) Viability of FL5.12 clones expressing HA-Bcl-y after withdrawal of IL-3. Cell viability was measured at the indicated times following cytokine withdrawal. Each data point represents the average of duplicate cultures assayed in parallel. Viability assays were repeated several times and results of a representative experiment are shown. Neo is a G418-resistant (G418$^r$) FL5.12 clone transfected with a plasmid encoding neomycin resistance only; yb2, yb3, and yb4 are individual G418$^r$ FL5.12 clones that express HA-Bcl-y.
Figure 9B:
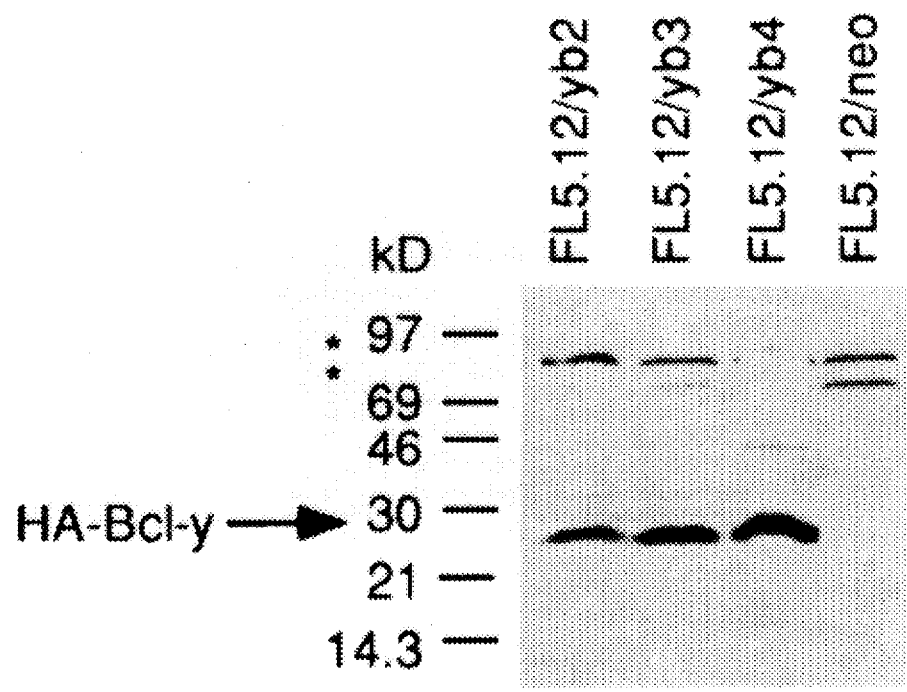
FIG. 9(B) Expression of HA-Bcl-y in FL5.12 cells. The HA-Bcl-y protein (~29 kD) was detected by Western blot analysis of extracts prepared from the indicated cell lines, with the HA-specific 12CA5 antibody. An asterix denotes non-specific bands.

To further test the function of Bcl-y in regulating apoptosis, the effect of Bcl-y expression in FL5.12 cells was investigated. A nine amino acid epitope from the influenza virus hemagglutinin antigen (HA) was engineered at the amino-terminus of Bcl-y to permit detection of the protein by the anti-HA monoclonal antibody 12CA5 (Kolodziej, P. A., et al., *Meth. Enzymol.* 194:508–519 (1991)). FL5.12 cells were transfected with a plasmid that directs the expression of HA-tagged Bcl-y from the CMV enhancer/promoter. Transfected cells were selected by virtue of their resistance to the drug G418, and expression of the HA-tagged Bcl-Y protein was detected by Western blot analysis with the anti-HA antibody 12CA5 (FIG. 9B). Several FL5.12 clones that expressed the highest levels of HA-Bcl-y were examined for viability under conditions of IL-3 deprivation, as previously described (Hockenbery, D., et al., *Nature* 348:334–336 (1990)). The FL5.12 clones expressing HA-Bcl-y (yb2, yb3, yb4) died at an increased rate relative to an FL5.12 clone transfected with the expression vector carrying only the neomycin resistance gene (FIG. 9A). Thus, in marked contrast to the protective effect of Bcl-2 expression in this cell line (Hockenbery, D., et al., *Nature* 348:334–336 (1990)), clones expressing Bcl-Y exhibited accelerated cell death upon IL-3 deprivation.

8. Bcl-Y expression counteracts the survival function of Bcl-2.

The ability of Bcl-Y to promote cell death upon withdrawal of IL-3 resembles the function of Bax, which has been shown to increase the rate of apoptosis in FL5.12 cells under the same conditions tested above (Oltvai, Z. N., et al., *Cell* 74:609–619 (1993)). Bax was also reported to counteract the enhanced survival provided by expression of Bcl-2 in FL5.12 cells. To further compare the activity of Bcl-Y to that of Bax, we asked whether expression of Bcl-Y would similarly overcome the inhibition of apoptosis afforded by expression of Bcl-2. FL5.12 cells were transfected with an expression plasmid carrying human Bcl-2 which provides substantial protection against cell death upon withdrawal of IL-3. To determine whether Bcl-Y could overcome this function of Bcl-2, the cells were infected with a recombinant retrovirus expression vector carrying the HA-tagged Bcl-y protein and the gene for puromycin resistance. For comparison, the FL5.12 cells expressing Bcl-2 were separately infected with a retrovirus carrying HA-tagged Bax, or a vector encoding puromycin resistance only.

Figure 10A:
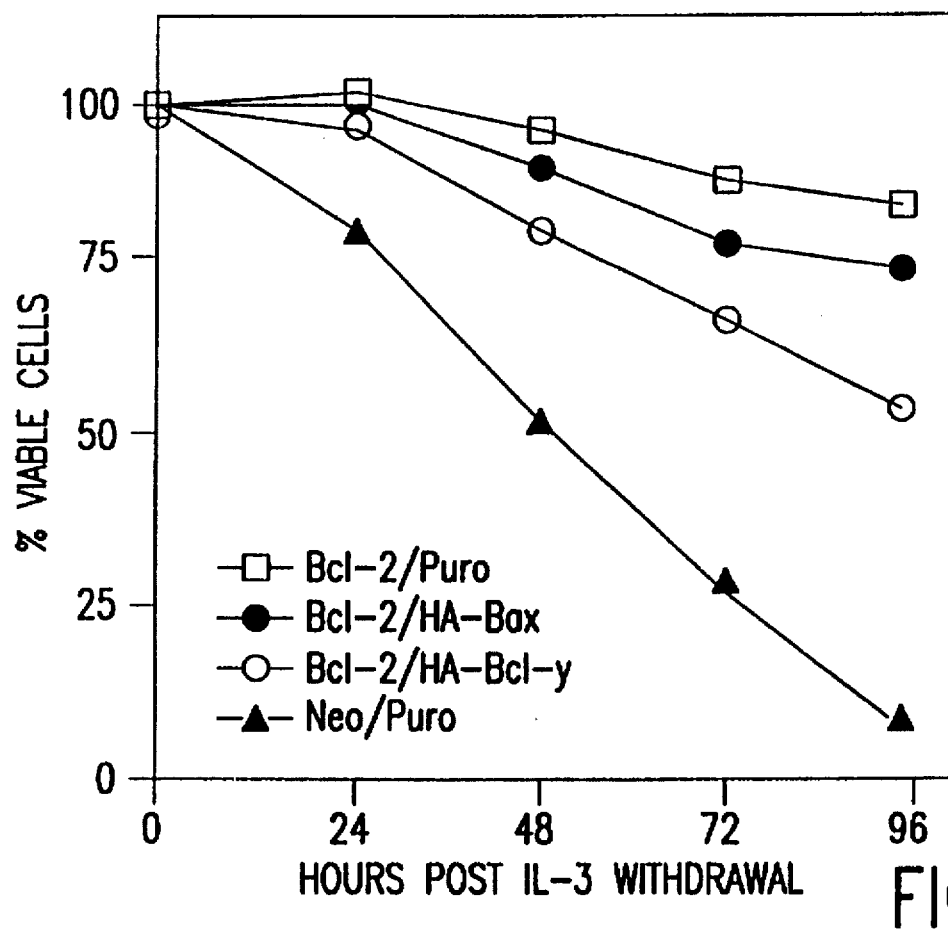
FIG. 10(A) Viability of FL5.12 cell populations expressing Bcl-2 in combination with either HA-Bcl-Y or HA-Bax following withdrawal of IL-3. Drug resistant cells that arose after infection of Bcl-2 expressing FL5.12 cells with retroviruses expressing HA-Bcl-Y, HA-Bax, or puromycin alone, were pooled and analyzed as cell populations. The neo/puro population is a G418$^r$ FL5.12 cell line that does not express exogenous Bcl-2, infected with the puromycin-encoding retrovirus vector alone.
Figure 10B:
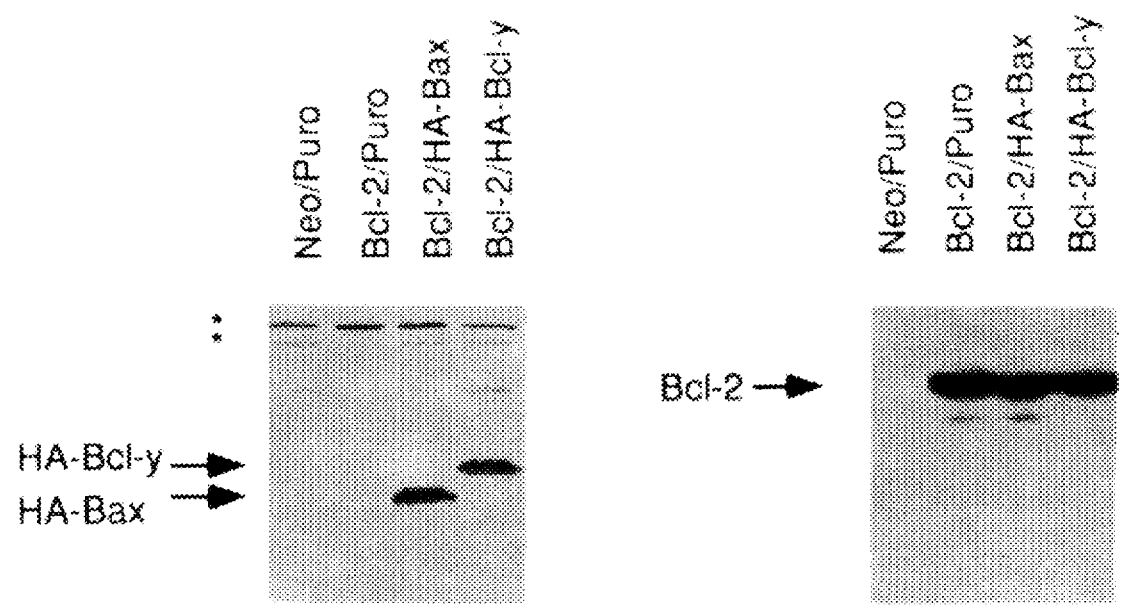
FIG. 10(B) Expression of HA-Bcl-Y, HA-Bax, and Bcl-2 in FL5.12 cell populations. Extracts were prepared from the indicated cell populations and HA-tagged proteins (left) and exogenous human Bcl-2 (right) were detected by Western blot analysis.

Pooled populations of puromycin-resistant cells expressing Bcl-2 (Bcl-2/puro population) were largely resistant to withdrawal of IL-3, reflecting the protective activity of Bcl-2 in these cells (FIG. 10A). Viability of the cell population expressing both Bcl-2 and HA-Bcl-y (Bcl-2/HA-Bcl-Y population) decreased faster, and to a greater extent, indicating that the protective function of Bcl-2 was partially overcome by Bcl-y in this cell population. As with Bcl-Y, expression of HA-Bax partly counteracted the prolonged survival provided by Bcl-2 (FIG. 10A). Thus, the effect of Bcl-Y on the survival of Bcl-2 expressing cells was as great or greater than that of Bax in this assay. Western blot analysis of these infected FL5.12 cell populations showed expression of HA-Bax and HA-Bcl-Y proteins (FIG. 10B). In addition, the increased sensitivity of cell populations expressing HA-Bcl-Y and HA-Bax to IL-3 withdrawal was not due to reduced levels of Bcl-2 (FIG. 10B).

Figure 11A:
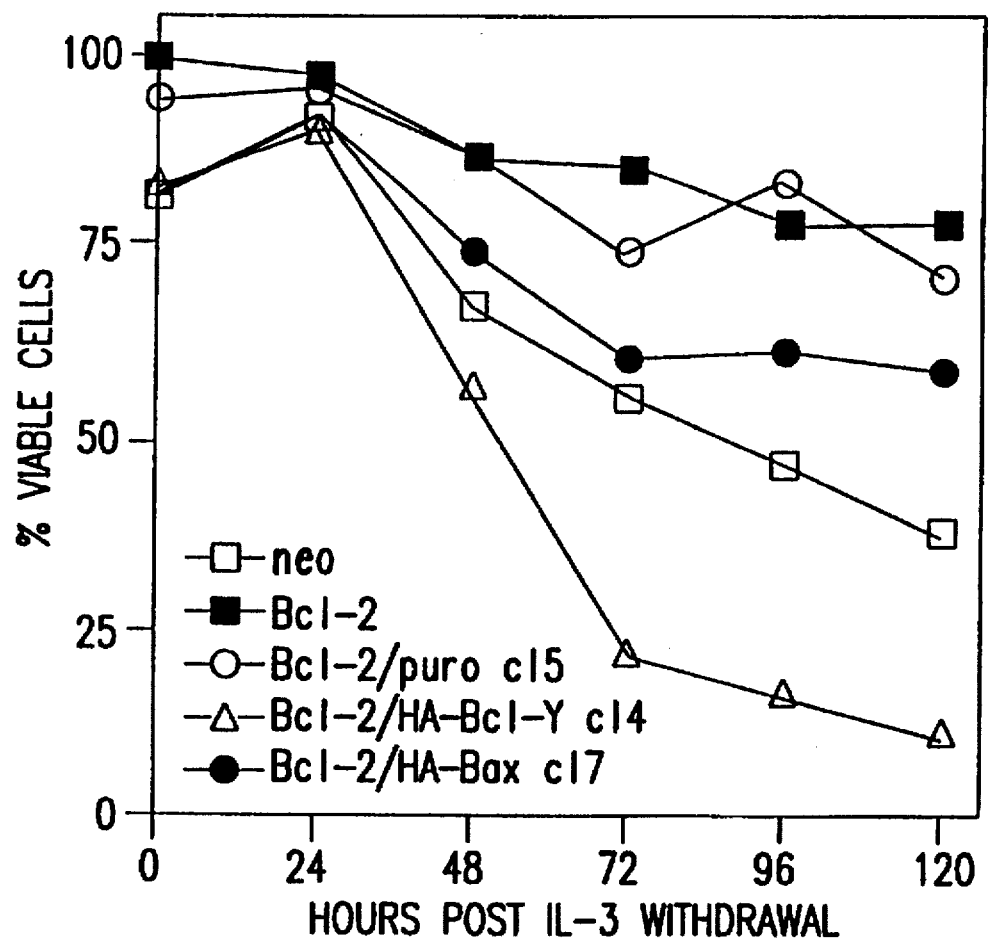
FIG. 11(A) Viability of FL5.12 clones expressing Bcl-2 in combination with either HA-Bcl-Y or HA-Bax following withdrawal of IL-3.
Figure 11B:
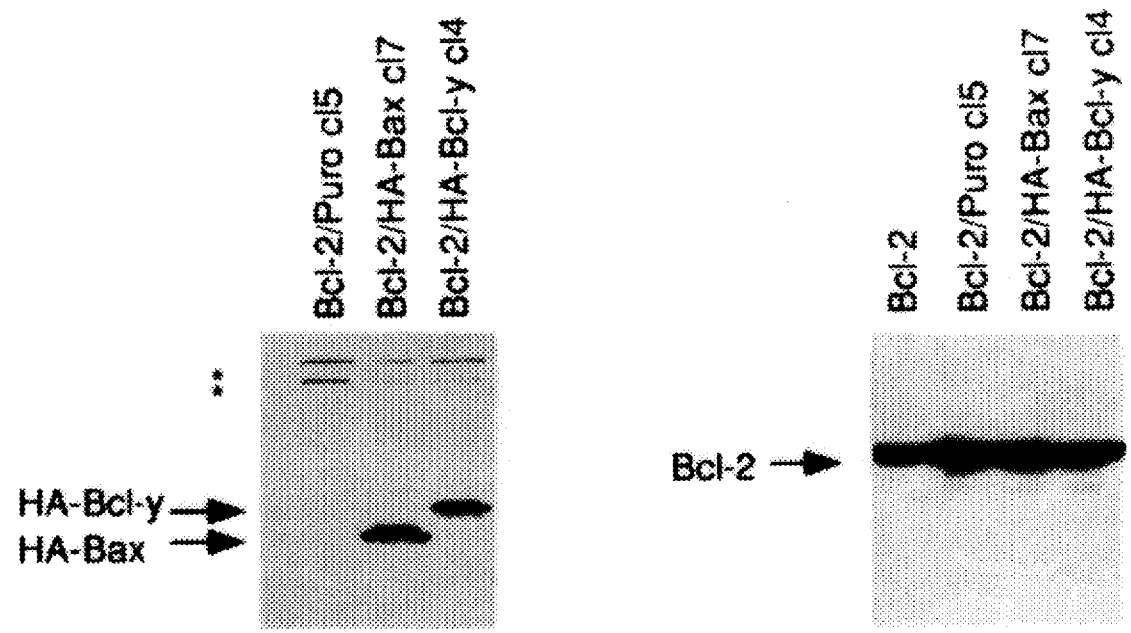
FIG. 11(B) Expression of HA-tagged proteins in FL5.12 clones. Ha-tagged proteins (left) and exogenous human Bcl-2 (right) were detected by Western blot analysis.

Additional experiments were performed by isolating individual clones expressing Bcl-2 in combination with either HA-Bax or HA-Bcl-Y from the retrovirus-infected cell populations described above. Clones expressing the highest levels of exogenous HA-Bcl-Y or HA-Bax showed a more complete inhibition of Bcl-2 function than the cell populations from which they were isolated (FIG. 11). Viablity of Bcl-2/HA-Bcl-Y c14 cells decreased more rapidly than a clone that did not express human Bcl-2 (neo, FIG. 11A), indicating that Bcl-2 function in this clone was totally abrogated by Bcl-Y expression. Again, Western blots demonstrated that similar levels of human Bcl-2 were expressed in the infected clones relative to the parental cell line (FIG. 11B).

These results demonstrate that enforced expression of Bcl-Y can overcome the survival function of Bcl-2 and restore sensitivity to signals that induce apoptosis (IL-3 withdrawal). There is experimental evidence to suggest that certain tumor cells may require continued function of Bcl-2 (or related genes) for their survival ((L. Campos, et al., *Blood* 84:595–600 (1994); J. C. Reed, et al., *Cancer Res.* 50:6565 (1990)). Introduction of Bcl-y, or a functional equivalent, into such tumor cells may restore sensitivity to signals that trigger apoptosis (i.e., deprivation of growth factors, treatment with chematherapeutic agents).

9. Bcl-Y interacts with Bcl-2 and Bcl-XL in vitro

It has been suggested that Bax may regulate Bcl-2 function through a specific protein/protein interaction (X. M. Yin, et al., *Nature* 369:321–323 (1994)). The inhibition of Bcl-2 function by Bcl-y may therefore also be dependent on a specific interaction between the two proteins. To test whether Bcl-y could interact with Bcl-2, glutathione S-transferase fusion proteins of Bcl-2 (GST-bcl-2) or its homolog Bcl-XL (GST- bcl-xl) were mixed with 35S-methionine-labeled HA-Bcl-Y generated by in vitro transcription/translation. Resulting complexes were captured on glutathione-agarose and analyzed by SDS-PAGE. HA-Bcl-Y clearly co-precipitated with GST-Bcl-2 and to an even greater extent with GST-bcl-xl. No interaction was observed when HA-bcl-y was incubated with GST alone. Therefore, bcl-y can specifically interact with bcl-2 and bcl-xl in vitro.

10. Chromosomal localization of the bcl-Y gene

Since multiple members of the Bcl-2 family may normally be responsible for regulating cell death, a variety of mutational alterations could potentially disrupt this control and contribute to tumor development. For example, activation of Bcl-2 expression by a chromosomal translocation contributes to the onset of follicular lymphoma. Analogous oncogenic lesions that suppress apoptosis could be generated, in principle, by the loss of a gene such as bcl-Y that opposes bcl-2 function, and/or positively regulates cell death. In this respect, bcl-Y may be viewed as a candidate tumor suppressor gene.

To analyze whether loss or mutation of bcl-y is a recurrent event in certain human tumors, the chromosomal location of the bcl-Y gene was determined. A fragment of human genomic DNA encompassing bcl-Y was isolated by screening a P1 phage library (Genomic Systems, Inc.). The bcl-Y genomic clone was used as a probe for fluorescent in situ hybridation to metaphase chromosomes (BIOS Laboratories). This analysis revealed that the bcl-Y genomic locus maps to the short arm of human chromosome 6 (6p21.3). Abnormalities of 6p21 have been detected in uterine leiomyomas (J. Mark, et al., *Cancer Genet. Cytogenet.* 44:1 (1990)), astrocytomas (B. C. Liang, et al., *Neurol.* 44:533–536), benign lipomas (N. Mandahl, et al., *Hum. Genet.* 79:203–208), ovarian cancers (W. Cliby, et al., *Cancer Res.* 53:2393–2398), and endometrial polyps (P. D. Cin, et al., *Gynec. Oncol.* 46:393–396). A large number of diseases have been shown to be associated with the MHC region, which also maps to 6p21 (J. L. Tiwari, and P. I. Terasaki, HLA and Disease Associations. New York: Springer-Verlag (1985)).

All publications mentioned in this specification are indicative of the level of the skill of those skilled in the art to which this invention pertains. All publications are herein incorporated by reference, to the same extent as if each individual publication was specifically and individually indicated to be incorporated by reference.

While the invention has been described in connection with the specific embodiments thereof, it will be understood that it is capable of further modifications and this application is intended to cover any variations, uses, or adoptions of the invention following, in general, principles of the invention and including such departures from the present disclosure as come within known or customary practice within the art to which the invention pertains and as may be applied to the essential features hereinbefore set forth and as follows in the scope of the appended claims.

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGGAAGATCT AANTGGGNN GNNTNGT                2 7

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCTTCTGCAG NAANNCTCCC ACCCC                          25

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCAGGATCCG CTTCGGGGCA AGGCCCAG                      28

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCGGAATTCG AGTCATGATT TGAAGAATC                    29

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Ala Tyr Pro Tyr Asp Val Pro Asp Tyr Ala Ser Leu Gly Ser
 1               5                  10                  15
```

( 2 ) INFORMATION FOR SEQ ID NO:6:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Glu Glu Leu Phe Arg Asp Gly Val Asn Trp Gly Arg Ile Val Ala Phe Phe
                 5                  10                  15
Glu Phe Gly Gly Val Met Cys Val Glu Ser Val Asn Arg Glu Met Ser Pro
            20                  25                  30
Leu Val Asp Asn Ile Ala Leu Trp Met Thr Glu Tyr Leu Asn Arg His Leu
```

```
                  3 5                           4 0                          4 5                        5 0

His  Thr  Trp  Ile  Gln  Asp  Asn  Gly  Gly  Trp  Asp  Ala  Phe  Val  Glu  Leu  Tyr
                          5 5                           6 0                         6 5
```

( 2 ) INFORMATION FOR SEQ ID NO:7:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asn  Glu  Leu  Phe  Arg  Asp  Gly  Val  Asn  Trp  Gly  Arg  Ile  Val  Ala  Phe  Phe
                    5                         1 0                        1 5

Ser  Phe  Gly  Gly  Ala  Leu  Cys  Val  Glu  Ser  Val  Asp  Lys  Glu  Met  Gln  Val
          2 0                        2 5                         3 0

Leu  Val  Ser  Arg  Ile  Ala  Ala  Trp  Met  Ala  Thr  Tyr  Leu  Asn  Asp  His  Leu
3 5                        4 0                        4 5                        5 0

Glu  Pro  Trp  Ile  Gln  Glu  Asn  Gly  Gly  Trp  Asp  Thr  Phe  Val  Glu  Leu  Tyr
               5 5                           6 0                       6 5
```

( 2 ) INFORMATION FOR SEQ ID NO:8:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ala  Asp  Met  Phe  Ser  Asp  Gly  Asn  Phe  Asn  Trp  Gly  Arg  Val  Val  Ala  Leu
                    5                         1 0                       1 5

Phe  Tyr  Phe  Ala  Ser  Lys  Leu  Val  Leu  Lys  Ala  Lys  Cys  Thr  Lys  Val  Pro
          2 0                        2 5                        3 0

Glu  Leu  Ile  Arg  Thr  Ile  Met  Gly  Trp  Thr  Leu  Asp  Phe  Leu  Arg  Glu  Arg
3 5                        4 0                        4 5                        5 0

Leu  Leu  Gly  Trp  Ile  Gln  Asp  Gln  Gly  Gly  Trp  Asp  Gly  Leu  Leu  Ser  Tyr
               5 5                           6 0                       6 5

Phe
```

( 2 ) INFORMATION FOR SEQ ID NO:9:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ile  His  Val  Phe  Ser  Asp  Gly  Val  Thr  Asn  Trp  Gly  Arg  Ile  Val  Thr  Leu
                    5                         1 0                       1 5

Ile  Ser  Phe  Gly  Ala  Phe  Val  Ala  Lys  His  Leu  Lys  Thr  Ile  Asn  Gln  Glu
          2 0                        2 5                        3 0

Ser  Cys  Ile  Glu  Pro  Leu  Ala  Glu  Ser  Ile  Thr  Asp  Val  Leu  Val  Arg  Thr
3 5                        4 0                        4 5                        5 0

Lys  Arg  Asp  Trp  Leu  Val  Lys  Gln  Arg  Gly  Trp  Asp  Gly  Phe  Val  Glu  Phe
```

Phe ( 2 ) INFORMATION FOR SEQ ID NO:10:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Glu  Lys  Glu  Phe  Glu  Asp  Gly  Ile  Ile  Asn  Trp  Gly  Arg  Ile  Val  Thr  Ile
               5                        10                         15

Phe  Ala  Phe  Gly  Gly  Val  Leu  Leu  Lys  Lys  Leu  Pro  Gln  Glu  Gln  Ile  Ala
          20                        25                        30

Leu  Asp  Val  Cys  Ala  Tyr  Lys  Gln  Val  Ser  Ser  Phe  Val  Ala  Glu  Phe  Ile
35                       40                        45                              50

Met  Asn  Asn  Thr  Gly  Glu  Trp  Ile  Arg  Gln  Asn  Gly  Gly  Trp  Glu  Asp  Gly
               55                        60                         65

Phe  Ile  Lys  Lys  Phe
70
```

( 2 ) INFORMATION FOR SEQ ID NO:11:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Thr  Glu  Leu  Phe  Lys  Asp  Leu  Ile  Asn  Trp  Gly  Arg  Ile  Cys  Gly  Phe  Ile
               5                        10                        15

Val  Phe  Ser  Ala  Arg  Met  Ala  Lys  Tyr  Cys  Lys  Asp  Ala  Asn  Asn  His  Leu
          20                        25                        30

Glu  Ser  Thr  Val  Ile  Thr  Thr  Ala  Tyr  Asn  Phe  Met  Lys  His  Asn  Leu  Leu
35                       40                        45                              50

Pro  Trp  Met  Ile  Ser  His  Gly  Gly  Gln  Glu  Glu  Phe  Leu  Ala  Phe  Ser
               55                        60                        65
```

( 2 ) INFORMATION FOR SEQ ID NO:12:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Leu  Glu  Ile  Phe  His  Arg  Gly  Asp  Pro  Ser  Leu  Gly  Arg  Ala  Leu  Ala  Trp
               5                        10                        15

Met  Ala  Trp  Cys  Met  His  Ala  Cys  Arg  Thr  Leu  Cys  Cys  Asn  Gln  Ser  Thr
          20                        25                        30

Pro  Tyr  Tyr  Val  Val  Asp  Leu  Ser  Val  Arg  Gly  Met  Leu  Glu  Ala  Ser  Glu
35                       40                        45                              50

Gly  Leu  Asp  Gly  Trp  Ile  His  Gln  Gln  Gly  Gly  Trp  Ser  Thr  Leu  Ile  Glu
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
AANTGGGGNN GNNTNGT                                              17
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
CCNCCNACCC TNCNNAAN                                             18
```

(2) INFORMATION FOR SEQ ID NO:15:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Asn Trp Gly Arg Val Val Ala Leu Leu Gly Phe Gly Tyr Arg Leu Ala
                  5                  10                  15
Leu His Val Tyr Gln His Gly Leu Thr Gly Phe Leu Gly Gln Val Thr
             20                  25                  30
Arg Phe Val Val Asp Phe Met Leu His His Cys Ile Ala Arg Trp Ile
         35                  40                  45
Ala Gln Arg Gly Gly Trp Asp Ala Phe
     50                  55
```

(2) INFORMATION FOR SEQ ID NO:16:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Ala Ser Gly Gln Gly Pro Gly Pro Pro Arg Gln Glu Cys Gly Glu
                  5                  10                  15
Pro Ala Leu Pro Ser Ala Ser Glu Glu Gln Val Ala Gln Asp Thr Glu
             20                  25                  30
Glu Val Phe Arg Ser Tyr Val Phe Tyr Arg His Gln Gln Glu Gln Glu
```

|       |       |       |       | 35    |       |       |       |       | 40    |       |       |       |       | 45    |       |       |       |
|-------|-------|-------|-------|-------|-------|-------|-------|-------|-------|-------|-------|-------|-------|-------|-------|-------|-------|
| Ala   | Glu   | Gly   | Val   | Ala   | Ala   | Pro   | Ala   | Asp   | Pro   | Glu   | Met   | Val   | Thr   | Leu   | Pro   |       |       |
|       | 50    |       |       |       |       | 55    |       |       |       |       | 60    |       |       |       |       |       |       |
| Leu   | Gln   | Pro   | Ser   | Ser   | Thr   | Met   | Gly   | Gln   | Val   | Gly   | Arg   | Gln   | Leu   | Ala   | Ile   |       |       |
| 65    |       |       |       |       | 70    |       |       |       |       | 75    |       |       |       |       | 80    |       |       |
| Ile   | Gly   | Asp   | Asp   | Ile   | Asn   | Arg   | Arg   | Tyr   | Asp   | Ser   | Glu   | Phe   | Gln   | Thr   | Met   | Leu   |       |
|       |       |       |       | 85    |       |       |       |       | 90    |       |       |       |       | 95    |       |       |       |
| Gln   | His   | Leu   | Gln   | Pro   | Thr   | Ala   | Glu   | Asn   | Ala   | Tyr   | Glu   | Tyr   | Phe   | Thr   | Lys   | Ile   |       |
|       |       |       | 100   |       |       |       |       | 105   |       |       |       |       | 110   |       |       |       |       |
| Ala   | Thr   | Ser   | Leu   | Phe   | Glu   | Ser   | Gly   | Ile   | Asp   | Trp   | Gly   | Arg   | Val   | Val   | Ala   | Leu   |       |
| 115   |       |       |       |       | 120   |       |       |       |       | 125   |       |       |       |       | 130   |       |       |
| Leu   | Gly   | Phe   | Gly   | Tyr   | Arg   | Leu   | Ala   | Leu   | His   | Val   | Tyr   | Gln   | His   | Gly   | Leu   | Thr   |       |
|       |       |       | 135   |       |       |       |       | 140   |       |       |       |       | 145   |       |       |       |       |
| Gly   | Phe   | Leu   | Gly   | Gln   | Val   | Thr   | Arg   | Phe   | Val   | Val   | Asp   | Phe   | Met   | Leu   | His   | His   |       |
|       | 150   |       |       |       |       | 155   |       |       |       |       | 160   |       |       |       |       | 165   |       |
| Cys   | Ile   | Ala   | Arg   | Trp   | Ile   | Ala   | Gln   | Arg   | Gly   | Gly   | Trp   | Val   | Ala   | Ala   | Leu   | Asn   |       |
|       |       |       | 170   |       |       |       |       | 175   |       |       |       |       | 180   |       |       |       |       |
| Leu   | Gly   | Asn   | Gly   | Pro   | Ile   | Leu   | Asn   | Val   | Leu   | Val   | Val   | Leu   | Gly   | Val   | Val   | Leu   |       |
|       |       | 185   |       |       |       |       | 190   |       |       |       |       | 195   |       |       |       |       |       |
| Leu   | Gly   | Gln   | Phe   | Val   | Val   | Arg   | Arg   | Phe   | Phe   | Lys   | Ser   |       |       |       |       |       |       |
| 200   |       |       |       |       | 205   |       |       |       |       | 210   |       |       |       |       |       |       |       |

( 2 ) INFORMATION FOR SEQ ID NO:17:

( i ) SEQUENCE CHARACTERISTICS:
        ( A ) LENGTH: 1968 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

| TGAGCCACCC | GGGTTGGGCC | AGGATCCCGG | CAGGCTGATC | CCGTCCTCCA | CTGAGACCTG | 60   |
|------------|------------|------------|------------|------------|------------|------|
| AAAAATGGCT | TCGGGGCAAG | GCCCAGGTCC | TCCCAGGCAG | GAGTGCGGAG | AGCCTGCCCT | 120  |
| GCCCTCTGCT | TCTGAGGAGC | AGGTAGCCCA | GGACACAGAG | GAGGTTTTCC | GCAGCTACGT | 180  |
| TTTTTACCGC | CATCAGCAGG | AACAGGAGGC | TGAAGGGGTG | GCTGCCCCTG | CCGACCCAGA | 240  |
| GATGGTCACC | TTACCTCTGC | AACCTAGCAG | CACCATGGGG | CAGGTGGGAC | GGCAGCTCGC | 300  |
| CATCATCGGG | GACGACATCA | ACCGACGCTA | TGACTCAGAG | TTCCAGACCA | TGTTGCAGCA | 360  |
| CCTGCAGCCC | ACGGCAGAGA | ATGCCTATGA | GTACTTCACC | AAGATTGCCA | CCAGCCTGTT | 420  |
| TGAGAGTGGC | ATCAATTGGG | GCCGTGTGGT | GGCTCTTCTG | GGCTTCGGCT | ACCGTCTGGC | 480  |
| CCTACACGTC | TACCAGCATG | GCCTGACTGG | CTTCCTAGGC | CAGGTGACCC | GCTTCGTGGT | 540  |
| CGACTTCATG | CTGCATCACT | GCATTGCCCG | GTGGATTGCA | CAGAGGGGTG | GCTGGGTGGC | 600  |
| AGCCCTGAAC | TTGGGCAATG | GTCCCATCCT | GAACGTGCTG | GTGGTTCTGG | GTGTGGTTCT | 660  |
| GTTGGGCCAG | TTTGTGGTAC | GAAGATTCTT | GAAATCATGA | CTCCCAAGGG | TGCCCTTTGG | 720  |
| GTCCGGGTTC | AGACCCCTGC | CTGGACTTAA | GCGAAGTCTT | TGCCTTCTCT | GTTCCCTTGC | 780  |
| AGGGGTCCCC | CCTCAAGAGT | ACAGAAGCTT | TAGCAAGTGT | GCACTCCAGC | TTCGGAGGGC | 840  |
| CCCTGCGTGG | GGGCCAGTCA | GGCTGCAGAG | GCACCTCAAC | ATTGCATGGT | GCTAGTGGGC | 900  |
| CCTCTCTCTG | GGCCCAGGGG | CTGTGGCCGT | CTCCTCCCTC | AGCTCTCTGG | GACCTCCTTA | 960  |
| GCCCTGTCTG | CTAGGCGCTG | GGGAGACTGA | TAACTTGGGG | AGGCAAGAGA | CTGGGAGCCA | 1020 |
| CTTCTCCCCA | GAAAGTGTTT | AACGGTTTTA | GCTTTTTATA | ATACCCTTGT | GAGAGCCCAT | 1080 |

```
TCCCACCATT CTACCTGAGG CCAGGACGTC TGGGGTGTGG GGATTGGTGG GTCTATGTTC    1140

CCCAGGATTC AGCTATTCTG GAAGATCAGC ACCCTAAGAG ATGGGACTAG GACCTGAGCC    1200

TGGTCCTGGC CGTCCCTAAG CATGTGTCCC AGGAGCAGGA CCTACTAGGA GAGGGGGGCC    1260

AAGGTCCTGC TCAACTCTAC CCCTGCTCCC ATTCCTCCCT CCGGCCATAC TGCCTTTGCA    1320

GTTGGACTCT CAGGGATTCT GGGCTTGGGG TGTGGGGTGG GGTGGAGTCG CAGACCAGAG    1380

CTGTCTGAAC TCACGTGTCA GAAGCCTCCA AGCCTGCCTC CCAAGGTCCT CTCAGTTCTC    1440

TCCCTTCCTC TCTCCTTATA GACACTTGCT CCCAACCCAT TCACTACAGG TGAAGGCTCT    1500

CACCCCATCC CTGGGGGCCT TGGGTGAGTG GCCTGCTAAG GCTCCTCCTT GCCCAGACTA    1560

CAGGGCTTAG GACTTGGTTT GTTATATCAG GGAAAAGGAG TAGGGAGTTC ATCTGGAGGG    1620

TTCTAAGTGG GAGAAGGACT ACCAACACCA CTAGGAATCC CAGAGGTGGG ATCCTCCCTC    1680

ATGGCTCTGG CACAGTGTAA TCCAGGGGTG TAGATGGGGG AACTGTGAAT ACTTGAACTC    1740

TGTTCCCCCA CCCTCCATGC TCCTCACCTG TCTAGGTCTC CTCAGGGTGG GGGGTGACAG    1800

TGCCTTCTCT ATTGGGCACA GCCTAGGGTC TTGGGGGTCA GGGGGGAGAA GTTCTTGATT    1860

CAGCCAAATG CAGGGAGGGG AGGCAGATGG AGCCCATAGG CCACCCCCTA TCCTCTGAGT    1920

GTTTGGAAAT AAACTGTGCA ATCCCCTCAC CCTGAAAAAA AAAAAAA                  1968
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Ala Ala Ser Arg Asp Pro Val Ala Arg Thr Ser Pro Leu Gln Thr Pro
              5                   10                  15
Ala Ala Pro Gly
        20
```

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Ala Ala Pro Ala Asp Pro Glu Met Val Thr Leu Pro Leu Gln Pro Ser
              5                   10                  15
Ser Thr Met Gly
        20
```

( 2 ) INFORMATION FOR SEQ ID NO:20:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Gly Asp Asp Phe Ser Arg Arg Tyr Arg Gly Asp Phe Ala Glu Met Ser
                  5                  10                 15

Ser Gln Leu His Leu Thr Pro Phe Thr Ala Arg Gly Arg Phe Ala Thr
             20                  25                 30

Val Val Glu Glu Leu Phe Arg Asp Gly Val Asn Trp Gly Arg Ile Val
         35                  40                  45

Ala Phe Phe Glu Phe Gly
     50

( 2 ) INFORMATION FOR SEQ ID NO:21:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Gly Asp Asp Ile Asn Arg Arg Tyr Asp Ser Glu Phe Gln Thr Met Leu
                  5                  10                 15

Gln His Leu Gln Pro Thr Ala Glu Asn Ala Tyr Glu Tyr Phe Thr Lys
             20                  25                 30

Ile Ala Thr Ser Leu Phe Glu Ser Gly Ile Asn Trp Gly Arg Val Val
         35                  40                  45

Ala Leu Leu Gly Phe Gly
     50

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Leu Asn Arg His Leu His Thr Trp Ile Gln Asp Asn Gly Gly Trp Asp
                  5                  10                 15

Ala Phe Val Glu Leu
         20

( 2 ) INFORMATION FOR SEQ ID NO:23:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Leu His His Cys Ile Ala Arg Trp Ile Ala Gln Arg Gly Gly Trp Val
                  5                  10                 15

Ala Ala Leu Asn Leu
         20

( 2 ) INFORMATION FOR SEQ ID NO:24:

( i ) SEQUENCE CHARACTERISTICS:
  ( A ) LENGTH: 49 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:24:

```
Val His Leu Ala Leu Arg Gln Ala Gly Asp Asp Phe Ser Arg Arg Tyr
                  5                   10                  15

Arg Gly Asp Phe Ala Glu Met Ser Ser Gln Leu His Leu Thr Pro Phe
            20                  25                  30

Thr Ala Arg Gly Arg Phe Ala Thr Val Val Glu Glu Leu Phe Arg Asp
        35                  40                  45

Gly
```

( 2 ) INFORMATION FOR SEQ ID NO:25:

( i ) SEQUENCE CHARACTERISTICS:
  ( A ) LENGTH: 49 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:25:

```
Val Gly Arg Gln Leu Ala Ile Ile Gly Asp Asp Ile Asn Arg Arg Tyr
                  5                   10                  15

Asp Ser Glu Phe Gln Thr Met Leu Gln His Leu Gln Pro Thr Ala Glu
            20                  25                  30

Asn Ala Tyr Glu Tyr Phe Thr Lys Ile Ala Thr Ser Leu Phe Glu Ser
        35                  40                  45

Gly
```

( 2 ) INFORMATION FOR SEQ ID NO:26:

( i ) SEQUENCE CHARACTERISTICS:
  ( A ) LENGTH: 49 amino a6cids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:26:

```
Val Lys Gln Ala Leu Arg Glu Ala Gly Asp Glu Phe Glu Leu Arg Tyr
                  5                   10                  15

Arg Arg Ala Phe Ser Asp Leu Thr Ser Gln Leu His Ile Thr Pro Gly
            20                  25                  30

Thr Ala Tyr Gln Ser Phe Glu Gln Val Val Asn Glu Leu Phe Arg Asp
        35                  40                  45

Gly
```

( 2 ) INFORMATION FOR SEQ ID NO:27:

( i ) SEQUENCE CHARACTERISTICS:
  ( A ) LENGTH: 45 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:27:

Leu Ser Glu Cys Leu Lys Arg Ile Gly Asp Glu Leu Asp Ser Asn Met
                5                   10                  15

Glu Leu Gln Arg Met Ile Ala Ala Val Asp Thr Asp Ser Pro Arg Val
            20                  25                  30

Phe Phe Arg Val Ala Ala Asp Met Phe Ser Asp Gly Asn
            35                  40                  45

( 2 ) INFORMATION FOR SEQ ID NO:28:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

Ala Leu Glu Thr Leu Arg Arg Val Gly Asp Gly Val Gln Arg Asn His
                5                   10                  15

Glu Thr Val Phe Gln Gly Asn Leu Arg Lys Leu Asp Ile Lys Asn Glu
            20                  25                  30

Asp Asp Val Lys Ser Leu Ser Arg Val Met Ile His Val Phe Ser Asp
            35                  40                  45

Gly Val
    50

( 2 ) INFORMATION FOR SEQ ID NO:29:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

Cys Arg Val Leu Gln Arg Val Ala Phe Ser Val Gln Lys Glu Val Glu
                5                   10                  15

Lys Asn Leu Lys Ser Tyr Leu Asp Asp Phe His Val Glu Ser Ile Asp
            20                  25                  30

Thr Ala Arg Ile Ile Phe Asn Gln Val Met Glu Lys Glu Phe Glu Asp
            35                  40                  45

Gly Ile
    50

( 2 ) INFORMATION FOR SEQ ID NO:30:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Gln Ile Lys Lys Ile Leu Thr Tyr Tyr Asp Glu Cys Leu Asn Lys Gln
                5                   10                  15

Val Thr Ile Thr Phe Ser Leu Thr Asn Ala Gln Glu Ile Lys Thr Gln
            20                  25                  30

```
Phe  Thr  Gly  Val  Val  Thr  Glu  Leu  Phe  Lys  Asp  Leu
          35                      40
```

(2) INFORMATION FOR SEQ ID NO:31:

(i) SEQUENCE CHARACTERISTICS:
      (A) LENGTH: 50 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:31:

```
Val  Val  Leu  Arg  Tyr  His  Val  Leu  Leu  Glu  Glu  Ile  Ile  Glu  Arg  Asn
                    5                        10                       15

Ser  Glu  Thr  Phe  Thr  Glu  Thr  Trp  Asn  Arg  Phe  Ile  Thr  His  Thr  Glu
               20                      25                       30

His  Val  Asp  Leu  Asp  Phe  Asn  Ser  Val  Phe  Leu  Glu  Ile  Phe  His  Arg
          35                      40                       45

Gly  Asp
     50
```

We claim:

1. An antibody capable of binding to a protein having the amino acid sequence as shown in FIG. 4, SEQ ID NO: 16, wherein said protein is human Bcl-Y protein.

2. An antibody capable of binding to a protein encoded by the nucleotide sequence as shown in FIG. 4, SEQ ID NO: 17, wherein said protein is human Bcl-Y protein.

3. The antibody of claims 1 or 2, wherein said antibody is selected from the group consisting of a polyclonal antibody and a monoclonal antibody.

4. The antibody of claim 3, wherein said antibody is a monoclonal antibody.

5. The antibody of claims 3 or 4, wherein said antibody is detectably labelled.

6. The antibody of claim 5, wherein said antibody is detectably labeled with a detectable label selected from the group consisting of a radiolabel, an enzyme label, a co-factor label, a fluorescent label, a paramagnetic label, a chemiluminescent label and a metal label.

* * * * *